US011352424B2

(12) United States Patent
Li et al.

(10) Patent No.: US 11,352,424 B2
(45) Date of Patent: Jun. 7, 2022

(54) ANTI-TIM-3 ANTIBODIES FOR COMBINATION WITH ANTI-PD-1 ANTIBODIES

(71) Applicants: Eli Lilly and Company, Indianapolis, IN (US); Innovent Biologics (Suzhou) Co. Ltd., Jiangsu (CN)

(72) Inventors: Yiwen Li, Woodcliff Lake, NJ (US); Yi Zhang, Edison, NJ (US)

(73) Assignees: Eli Lilly and Company, Indianapolis, IN (US); Innovent Biologics (Suzhou) Co. Ltd., Jiangsu (CN)

( * ) Notice: Subject to any disclaimer, the term of this patent is extended or adjusted under 35 U.S.C. 154(b) by 327 days.

(21) Appl. No.: 16/346,922

(22) PCT Filed: Dec. 4, 2017

(86) PCT No.: PCT/US2017/064480
§ 371 (c)(1),
(2) Date: May 2, 2019

(87) PCT Pub. No.: WO2018/106588
PCT Pub. Date: Jun. 4, 2018

(65) Prior Publication Data

US 2019/0276534 A1 Sep. 12, 2019

Related U.S. Application Data

(60) Provisional application No. 62/431,480, filed on Dec. 8, 2016.

(51) Int. Cl.

| | |
|---|---|
| ***C07K 16/28*** | (2006.01) |
| ***A61K 39/395*** | (2006.01) |
| ***A61K 45/06*** | (2006.01) |
| ***A61N 5/10*** | (2006.01) |
| ***A61K 39/00*** | (2006.01) |

(52) U.S. Cl.
CPC .... *C07K 16/2803* (2013.01); *A61K 39/39541* (2013.01); *A61K 45/06* (2013.01); *A61N 5/10* (2013.01); *C07K 16/2818* (2013.01); *A61K 2039/505* (2013.01); *C07K 2317/21* (2013.01); *C07K 2317/24* (2013.01); *C07K 2317/34* (2013.01); *C07K 2317/565* (2013.01); *C07K 2317/76* (2013.01); *C07K 2317/92* (2013.01)

(58) Field of Classification Search
CPC ............ C07K 16/2803; C07K 16/2818; A61K 39/39541; A61K 45/06; A61N 5/10
See application file for complete search history.

(56) References Cited

U.S. PATENT DOCUMENTS

| | | | | |
|---|---|---|---|---|
| 8,697,069 | B2 | 4/2014 | Kuchroo et al. | |
| 10,253,096 | B2 | 4/2019 | Zhang et al. | |
| 10,508,149 | B2 * | 12/2019 | Kehry ................ | C07K 16/2809 |
| 2012/0189617 | A1 | 7/2012 | Takayanagi et al. | |
| 2014/0044728 | A1 | 2/2014 | Takayanagi et al. | |
| 2017/0044260 | A1 | 2/2017 | Baruah et al. | |

FOREIGN PATENT DOCUMENTS

| | | |
|---|---|---|
| CN | 103721255 | 4/2014 |
| WO | 2011159877 | 12/2011 |
| WO | 2013006490 | 1/2013 |
| WO | 2014179664 | 11/2014 |
| WO | 2015117002 | 8/2015 |
| WO | 2016007513 | 1/2016 |
| WO | 2016161270 | 10/2016 |
| WO | 2018039020 | 3/2018 |

OTHER PUBLICATIONS

The Merck Manuals Online Medical Library, [online]. Merck Research Laboratories, 2006-2007. [retrieved on Oct. 19, 2020]. < URL: https://www.merckmanuals.com/professional/hematology-and-oncology/overview-of-cancer/cellular-and-molecular-basis-of-cancer >. Cellular and Molecular Basis of Cancer (Year: 2007).*

Fourcade et al. "Upregulation of Tim-3 and PD-1 expression is associated with tumor antigen-specific CD8+ T cell dysfunction in melanoma patients", J Exp Med. Sep. 27, 2010;207(10):2175-86 (Year: 2010).*

Kim, et al., "Combination Therapy with Anti-PD-1, Anti-TIM-3, and Focal Radiation Results in Regression of Murine Gliomas," Clinical Cancer Research, vol. 23, No. 1, pp. 124-136 (2016).

Koyama, et al. "Adaptive resistance to therapeutic PD-1 blockade is associated with upregulation of alternative immune checkpoints," Nature Communications, vol. 7, No. 17, p. 10501, XP055309591 (Feb. 17, 2016).

Nglow, et al., "Anti-TIM3 Antibody Promotes T Cell 1FN-?-Mediated Antitumor Immunity and Suppresses Established Tumors," Cancer Research, vol. 71, No. 10, pp. 3540-3551, XP055181433, (Mar. 23, 2011).

Zong, et al., "Identification of Co-inhibitory Receptors PD-1 and TIM-3 on T Cells from Gastric Cancer Patients," Immunotherapy: Open Access, vol. 01, No. 01, the whole document (Jan. 1, 2016).

International Search Report for PCT/US2017/064480.

Written Opinion for PCT/US2017/064480.

Anderson, "Tim-3: Emerging Target in the Cancer Immunotherapy Landscape," Cancer Immunology Research, vol. 2, No. 5, pp. 393-398 (2014).

* cited by examiner

*Primary Examiner* — Daniel E Kolker
*Assistant Examiner* — Peter Johansen
(74) *Attorney, Agent, or Firm* — Grant Reed

(57) ABSTRACT

The present invention relates to antibodies that bind human T-cell immunoglobulin- and mucin-domain-containing protein-3 (Tim-3), and may be useful for treating solid and hematological tumors in combination with anti-human PD-1 antibodies, chemotherapy, and ionizing radiation.

11 Claims, No Drawings

Specification includes a Sequence Listing.

ANTI-TIM-3 ANTIBODIES FOR COMBINATION WITH ANTI-PD-1 ANTIBODIES

The present invention is in the field of medicine. Particularly, the present invention relates to antibodies directed to human T-cell immunoglobulin- and mucin-domain-containing protein-3 (Tim-3) (SEQ ID NO: 1) that can be combined with antibodies directed to human PD-1 (SEQ ID NO: 34), compositions comprising such anti-human Tim-3 antibodies or anti-human PD-1 antibodies, and methods of using such anti-human Tim-3 antibodies in combination with anti-human PD-1 antibodies for the treatment of solid and hematological tumors alone or in further combination with chemotherapy, ionizing radiation, and other cancer therapeutics.

Tumor cells escape detection and elimination by the immune system through multiple mechanisms some of which include the manipulation of immune checkpoint pathways. Immune checkpoint pathways are used in self-tolerance maintenance and in the regulation of T cell activation, but cancer cells can manipulate these pathways to prolong tumor survival. The PD-1/human programmed cell death 1 ligand 1 (PD-L1) pathway is one such immune checkpoint. Human PD-1 (SEQ ID NO: 34) is expressed on T cells, and the binding of PD-L1 or PD-L2 to PD-1 has been shown to inhibit T cell proliferation and cytokine production. Moreover, some tumors are known to express PD-L1 and PD-L2 and such expression can contribute to the inhibition of the intratumoral immune response.

In addition to the PD-1/PD-L1 pathway, T cells recognizing tumor antigens can also express other checkpoint receptors, such as Tim-3. In particular, T cells expressing Tim-3 can exhibit an exhausted phenotype characterized by an impairment in cytotoxic functions, effector cytokine production, and proliferation. In this regard, it has been shown that anti-Tim-3 antibodies can restore anti-tumor immunity in some murine cancer models. Moreover, it has also been shown that some patients who develop adaptive resistance to anti-PD-1 treatment display an upregulation of Tim-3 on their T cells.

Antibodies directed to human Tim-3 are known. Humanized antibodies against human Tim-3 are described in WO15117002. MBG453, an anti-human Tim-3 antibody, is currently being tested in human clinical trials as a single agent and in combination with an anti-human PD-1 antibody. However, no antibody targeting Tim-3 has been approved for therapeutic use in humans nor has any anti-human Tim-3 antibody been shown to display efficacy against human tumors when combined with an anti-human PD-1 antibody. Thus, there remains a need for anti-human Tim-3 antibodies that can be combined with anti-human PD-1 antibodies as well as other therapies for treating human cancers.

Tim-3 (SEQ ID NO:1) has been shown to interact with galectin-9 (SEQ ID NO:15), phosphaditylserine ($C_{13}H_{24}NO_{10}P$), high-mobility group Box 1 (HMGB1), and carcinoembryonic antigen cell adhesion molecule 1 (CEACAM1) (SEQ ID NO:14). Because all of the aforementioned Tim-3 ligands are not exclusive ligands of Tim-3, it is desirable to provide therapeutic anti-Tim-3 antibodies that differentially block the activity of said ligands as these ligands can regulate the immune system independently of Tim-3. Such a strategy can provide alternative ways to more specifically modulate Tim-3 activity, allowing for tailored immuno-oncology based therapies for patients. Furthermore, such anti-Tim-3 antibodies can provide options for combinatorial therapies with anti-human PD-1 antibodies. Thus, there also remains a need to provide antibodies that bind human Tim-3 and inhibit Tim-3's interactions with some of Tim-3's ligands, but not others, and that can be combined with anti-human PD-1 antibodies.

The anti-human Tim-3 antibodies described herein can block human Tim-3 (SEQ ID NO: 1) from binding to human galectin-9 (SEQ ID NO:15) and phosphatidylserine while simultaneously not blocking the binding of human Tim-3 and human CEACAM1 (SEQ ID NO:14). Surprisingly, the anti-Tim-3 antibodies of the present invention can be combined with an anti-human PD-1 antibody to enhance tumor clearance. Surprisingly, the anti-Tim-3 antibodies described herein block human Tim-3 interactions with phosphatidylserine ($C_{13}H_{24}NO_{10}P$) and galectin-9 (SEQ ID NO:15), but not human Tim-3's interactions with CEACAM1 (SEQ ID NO:14) and can be combined with an anti-human PD-1 antibody to treat cancer.

While antibodies targeting PD-1 (SEQ ID NO:34) for cancer immunotherapy have proven effective for some cancers, some cancers become less sensitive to PD-1 therapy over time or do not respond at all. In some embodiments, the present invention provides an anti-human Tim-3 antibody that can be administered to patients who have progressed or are progressing under anti-human PD-1 antibody therapy. In some embodiments, the present invention provides an anti-human Tim-3 antibody that can be administered in combination with an anti-human PD-1 antibody to patients who have no previously received anti-human PD-1 antibody therapy.

The present invention includes anti-human Tim-3 (SEQ ID NO: 1) antibodies comprising HCDR1, HCDR2, HCDR3, LCDR1, LCDR2, and LCDR3 consisting of the amino acid sequences of SEQ ID NOs: 2, 3, 4, 5, 6, and 7, respectively; a heavy chain variable region having the amino acid sequence of SEQ ID NO: 8 and a light chain variable region having the amino acid sequence of SEQ ID NO: 9; and/or a heavy chain having the amino acid sequence of SEQ ID NO: 10 and a light chain having the amino acid sequence of SEQ ID NO: 11 for simultaneous, separate, or sequential combination with an anti-human PD-1 antibody.

Non-limiting examples of known anti-human PD-1 antibodies include PDR001 (described in US20150210769; CAS registry number 1859072-53-9), MEDI0680, REGN2810, BGB-A317, nivolumab (CAS registry number 946414-94-4; wherein nivolumab comprises a heavy chain having the amino acid sequence of SEQ ID NO: 30 and a light chain having the amino acid sequence of SEQ ID NO: 31), and pembrolizumab (CAS registry number 137-4853-91-4; wherein pembrolizumab comprises a heavy chain having the amino acid sequence of SEQ ID NO: 32 and a light chain having the amino acid sequence of SEQ ID NO: 33). Furthermore, said known anti-human PD-1 antibodies can be expressed in a variety of cell lines and produced via various manufacturing processes and may exhibit some difference(s) as a result.

Non-limiting examples of other anti-human PD-1 (SEQ ID NO: 34) antibodies include anti-human PD-1 antibodies comprising at least one of the following: (a) HCDR1 having the amino acid sequence of SEQ ID: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody is PDR001, REGN2810, MEDI0680, BGB-A317, nivolumab, or pembrolizumab.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody is PDR001, REGN2810, MEDI0680, BGB-A317, nivolumab, or pembrolizumab.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody is PDR001, REGN2810, MEDI0680, BGB-A317, nivolumab, or pembrolizumab.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: a heavy chain having the amino acid sequence of SEQ ID NO: 24 and a light chain having the amino acid sequence of SEQ ID NO: 26.

A method of treating cancer comprising administering to a patient in need, thereof an effective amount of an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 25 and a light chain having the amino acid sequence of SEQ ID NO: 26.

A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is lung cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the lung cancer is non-small cell lung cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is head and neck cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is colorectal cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is pancreatic cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is gastric cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is kidney cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is bladder cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is prostate cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is breast cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is ovarian cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is esophageal cancer. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is soft tissue sarcoma. A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is liver cancer.

A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; wherein at least one of the anti-human Tim-3 antibody and anti-human PD-1 antibody is administered in simultaneous, separate, or sequential combination with ionizing radiation and/or one or more chemotherapeutic agents.

A method of treating cancer comprising administering to a patient in need, thereof an effective amount of an anti-human Tim-3 (SEQ ID NO: 1) antibody of the present invention in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26; wherein at least one of the anti-human Tim-3 antibody and anti-human PD-1 antibody is administered in simultaneous, separate, or sequential combination with ionizing radiation and/or one or more chemotherapeutic agents.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody is PDR001, REGN2810, MEDI0680, BGB-A317, nivolumab, or pembrolizumab.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody is PDR001, REGN2810, MEDI0680, BGB-A317, nivolumab, or pembrolizumab.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody is PDR001, REGN2810, MEDI0680, BGB-A317, nivolumab, or pembrolizumab.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

An anti-human Tim-3 (SEQ ID NO: 1) antibody of the present invention for use in simultaneous, separate, or sequential combination with anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 24 and a light chain having the amino acid sequence of SEQ ID NO: 26.

An anti-human Tim-3 (SEQ ID NO: 1) antibody of the present invention for use in simultaneous, separate, or sequential combination with an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 25 and a light chain having the amino acid sequence of SEQ ID NO: 26.

An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. An effective amount of an anti-human Tim-3 (SEQ ID NO: 1) antibody of the present invention for use in simultaneous, separate, or sequential combination with an effective amount of an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is lung cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the lung cancer is non-small cell lung cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is head and neck cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is colorectal cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is pancreatic cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is gastric cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is kidney cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is bladder cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is prostate cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is breast cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is ovarian cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is esophageal cancer. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is soft tissue sarcoma. An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; and wherein the cancer is liver cancer.

An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; wherein at least one of the anti-human Tim-3 antibody and anti-human PD-1 antibody is administered in simultaneous, separate, or sequential combination with ionizing radiation and/or one or more chemotherapeutic agents.

An anti-human Tim-3 (SEQ ID NO: 1) antibody of the present invention for use in simultaneous, separate, or sequential combination with an anti-human PD-1 (SEQ ID NO: 34) antibody; optionally, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26; wherein at least one of the anti-human Tim-3 antibody and anti-human PD-1 antibody is administered in simultaneous, separate, or sequential combination with ionizing radiation and/or one or more chemotherapeutic agents.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain variable region having the amino acid sequence of SEQ ID NO: 8 and a light chain variable region having the amino acid sequence of SEQ ID NO: 9.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain having the amino acid sequence of SEQ ID NO: 10 and a light chain having the amino acid sequence of SEQ ID NO: 11.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody is PDR001, REGN2810, MEDI0680, BGB-A317, nivolumab, or pembrolizumab.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody is PDR001, REGN2810, MEDI0680, BGB-A317, nivolumab, or pembrolizumab.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody is PDR001, REGN2810, MEDI0680, BGB-A317, nivolumab, or pembrolizumab.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain variable region having the amino acid sequence of SEQ ID NO: 8 and a light chain variable region having the amino acid sequence of SEQ ID NO: 9; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 24 and a light chain having the amino acid sequence of SEQ ID NO: 26.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 25 and a light chain having the amino acid sequence of SEQ ID NO: 26.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is lung cancer. 1. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is melanoma. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the lung cancer is non-small cell lung cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is head and neck cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is colorectal cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is pancreatic cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is gastric cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is kidney cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is bladder cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is prostate cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is breast cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is ovarian cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is esophageal cancer. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is soft tissue sarcoma. Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; and wherein the cancer is liver cancer.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; wherein at least one of the anti-human Tim-3 antibody and anti-human PD-1 antibody is administered in simultaneous, separate, or sequential combination with ionizing radiation and/or one or more chemotherapeutic agents.

Use of an anti-human Tim-3 (SEQ ID NO:1) antibody for the manufacture of a medicament for the treatment of cancer, wherein the medicament is to be administered simultaneously, separately, or sequentially with and an anti-human PD-1 (SEQ ID NO: 34) antibody, optionally, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26; wherein at least one of the anti-human Tim-3 antibody and anti-human PD-1 antibody is administered in simultaneous, separate, or sequential combination with ionizing radiation and/or one or more chemotherapeutic agents.

A kit for the treatment of cancer, the kit comprising a first pharmaceutical composition comprising an anti-human Tim-3 (SEQ ID NO:1) antibody of the present invention and a second pharmaceutical composition comprising an anti-human PD-1 (SEQ ID NO: 34) antibody. A kit for the treatment of cancer, the kit comprising a first pharmaceutical composition comprising an anti-human Tim-3 (SEQ ID NO:1) antibody of the present invention and a second pharmaceutical composition comprising an anti-human PD-1 (SEQ ID NO: 34) antibody; wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

A kit for the treatment of cancer, the kit comprising a first pharmaceutical composition comprising an anti-human Tim-3 (SEQ ID NO:1) antibody and a second pharmaceutical composition comprising an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11.

A kit for the treatment of cancer, the kit comprising a first pharmaceutical composition comprising an anti-human Tim-3 (SEQ ID NO:1) antibody and a second pharmaceutical composition comprising an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody is PDR001, REGN2810, MEDI0680, BGB-A317, nivolumab, or pembrolizumab.

A kit for the treatment of cancer, the kit comprising a first pharmaceutical composition comprising an anti-human Tim-3 (SEQ ID NO:1) antibody and a second pharmaceutical composition comprising an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A kit for the treatment of cancer, the kit comprising a first pharmaceutical composition comprising an anti-human Tim-3 (SEQ ID NO:1) antibody and a second pharmaceutical composition comprising an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A kit for the treatment of cancer, the kit comprising a first pharmaceutical composition comprising an anti-human Tim-3 (SEQ ID NO:1) antibody and a second pharmaceutical composition comprising an anti-human PD-1 (SEQ ID NO: 34) antibody; wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 25 and a light chain having the amino acid sequence of SEQ ID NO: 26.

An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14). An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human Tim-3 antibody also blocks binding of human Tim-3 to human galectin-9 (SEQ ID: 15).

An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer. An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human Tim-3 antibody also blocks binding of human Tim-3 to human galectin-9 (SEQ ID: 15); wherein the cancer is melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer.

An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human PD-1 antibody is PDR001, REGN2810, MEDI0680, BGB-A317, nivolumab, or pembrolizumab. An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human Tim-3 antibody also blocks binding of human Tim-3 to human galectin-9 (SEQ ID: 15); wherein the anti-human PD-1 antibody is PDR001, REGN2810, MEDI0680, BGB-A317, nivolumab, or pembrolizumab.

An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26. An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody blocks binding of human Tim-3 to human phosphatidylserine, but does not block binding of human Tim-3 to human CEACAM1 (SEQ ID: 14); wherein the anti-human Tim-3 antibody also blocks binding of human Tim-3 to human galectin-9 (SEQ ID: 15); wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody contacts at least one amino acid residue of the following on human Tim-3 (SEQ ID NO:1): 50, 55, 62-65 (inclusive), 72, 111, and 113-118 (inclusive). An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody contacts at least one amino acid residue of the following on human Tim-3 (SEQ ID NO:1): 50, 55, 62-65 (inclusive), 72, 111, and 113-118 (inclusive); wherein the anti-human Tim-3 antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues. An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody contacts at least one amino acid residue of the following on human Tim-3 (SEQ ID NO:1): 50, 55, 62-65 (inclusive), 72, 111, and 113-118 (inclusive); wherein the anti-human Tim-3 antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the anti-human Tim-3 antibody further contacts at least one residue of the following: 56-61 (inclusive), 107, 119-120 (inclusive), and 122. An anti-human Tim-3 (SEQ ID NO:1) antibody for use in simultaneous, separate, or sequential combination with an anti-human PD-1 (SEQ ID NO: 34) antibody, in the treatment of cancer, wherein the anti-human Tim-3 antibody contacts at least one amino acid residue of the following on human Tim-3 (SEQ ID NO:1): 50, 55, 62-65 (inclusive), 72, 111, and 113-118 (inclusive); wherein the anti-human Tim-3 antibody contacts: at least two of the residues; preferably at least three of the residues; more preferably at least four of the residues; more preferably at least five of the residues; more preferably at least six of the residues; more preferably at least seven of the residues; more preferably at least eight of the residues; more preferably at least nine of the residues; more preferably at least ten of the residues; more preferably at least eleven of the residues; more preferably at least twelve of the residues; more preferably at least thirteen of the residues; or more preferably all of the residues; wherein the anti-human Tim-3 antibody further contacts at least one residue of the following: 56-61 (inclusive), 107, 119-120 (inclusive), and 122; wherein the residues in contact are within six (6) angstroms or less of the anti-human Tim-3 antibody, as determined by X-ray crystallography.

A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11. A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody is PDR001, REGN2810, MEDI0680, BGB-A317, nivolumab, or pembrolizumab. A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11. A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises: (a) HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21; (b) a heavy chain variable region having the amino acid sequence of SEQ ID NO: 22 and a light chain variable region having the amino acid sequence of SEQ ID NO: 23; (c) a heavy chain having the amino acid sequence of SEQ ID NO: 24 and a light chain having the amino acid sequence of SEQ ID NO: 26; or (d) a heavy chain having the amino acid sequence of SEQ ID NO: 25 and a light chain having the amino acid sequence of SEQ ID NO: 26.

A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 24 and a light chain having the amino acid sequence of SEQ ID NO: 26.

A first pharmaceutical composition comprising an anti-human Tim-3 (SEQ ID NO:1) antibody for use in simultaneous, separate, or sequential combination with a second pharmaceutical composition comprising an anti-human PD-1 (SEQ ID NO: 34) antibody, in the treatment of cancer, wherein the anti-human Tim-3 antibody comprises a heavy chain having the amino acid sequence of SEQ ID NO: 10 and a light chain having the amino acid sequence of SEQ ID NO: 11; wherein the anti-human PD-1 antibody comprises a heavy chain having the amino acid sequence of SEQ ID NO: 25 and a light chain having the amino acid sequence of SEQ ID NO: 26.

The antibodies of the present invention are engineered, non-naturally occurring polypeptide complexes. A DNA molecule of the present invention is a non-naturally occurring DNA molecule that comprises a polynucleotide sequence encoding a polypeptide having the amino acid sequence of one of the polypeptides in an antibody of the present invention.

The antibodies of the present invention are an IgG type antibody and have "heavy" chains and "light" chains that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, certain anti-Tim-3 antibodies described herein contain an Fc portion that is derived from human IgG1. IgG1 is well known to bind to the proteins of the Fc-gamma receptor family (FcγR) as well as C1q. Interaction with these receptors can induce antibody-dependent cell cytotoxicity (ADCC) and complement-dependent cytotoxicity (CDC). Therefore, optionally, certain anti-Tim-3 antibodies described herein are a fully human monoclonal antibody lacking Fc effector function (IgG1, Fc-null). To achieve an Fc-null IgG1 antibody, selective mutagenesis of residues is necessary within the CH2 region of its IgG1 Fc region. Amino acid substitutions L234A, L235E, and G237A are introduced into IgG1 Fc to reduce binding to FcγRI, FcγRIIa, and FcγRIII, and substitutions A330S and P331S are introduced to reduce C1q-mediated complement fixation. To reduce the potential induction of an immune response when dosed in humans, certain amino acids may require back-mutations to match antibody germline sequences.

Optionally, the anti-human PD-1 antibodies of the present invention can contain an Fc portion which is derived from human $IgG_4$ Fc region because of a reduced ability to engage Fc receptor-mediated inflammatory mechanisms or to activate complement resulting in reduced effector function. Certain anti-human PD-1 antibodies of the present invention contain an $IgG_4$-Fc portion that has a serine to proline mutation at position 228. Further, certain anti-human PD-1 antibodies of the present invention contain an $IgG_4$-PAA Fc portion. The $IgG_4$-PAA Fc portion has a serine to proline mutation at position 228, a phenylalanine to alanine mutation at position 234, and a leucine to alanine mutation at position 235. The S228P mutation is a hinge mutation that prevents half-antibody formation (phenomenon of dynamic exchange of half-molecules in $IgG_4$ antibodies). The F234A and L235A mutations further reduce effector function of the already low human $IgG_4$ isotype. Further, certain anti-human PD-1 antibodies of the present invention contain an $IgG_4$-PAA Fc portion with the C-terminal lysine removed (des-Lys) from the heavy chain.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, the North CDR definitions are used.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a human kappa or lambda constant region. Preferably for anti-human Tim-3 antibodies of the present invention, the light chain constant region is a human kappa constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present invention may readily be produced in mammalian cells, non-limiting examples of which includes CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, NY (1994).

In other embodiments of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibodies of the present invention, or pharmaceutical compositions comprising the same, may be administered by parenteral routes (e.g., subcutaneous and intravenous). The antibodies of the present invention may be administered to a patient along with pharmaceutically acceptable carriers, diluents, or excipients in single or multiple doses. Pharmaceutical compositions of the present invention can be prepared by methods well known in the art (e.g., *Remington: The Science and Practice of Pharmacy,* $22^{nd}$ ed. (2012), A. Loyd et al., Pharmaceutical Press) and comprise an antibody, as disclosed herein, and one or more pharmaceutically acceptable carriers, diluents, or excipients.

Dosage regimens may be adjusted to provide the optimum desired response (e.g., a therapeutic effect). Treatment dosages may be titrated to optimize safety and efficacy. Dosing schedules, for intravenous (i.v.) or non-intravenous administration, localized or systemic, or combinations, thereof will typically range from a single bolus dosage or continuous infusion to multiple administrations per day (e.g., every 4-6 hours), or as indicated by the treating physician and the patient's condition.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

ANTIBODY GENERATION, EXPRESSION, AND PURIFICATION

The antibodies of the present invention may be generated by known methods including, but not limited to, by using phage display, transgenic animals, and/or humanization. For generation of anti-human Tim-3 antibodies, the human Tim-3 protein can be pretreated with PNGaseF enzyme prior to use. Additionally, the antibodies derived as described above may be further screened using the assays described herein.

The polypeptides of the variable regions of the heavy chain and light chain, the complete heavy chain and light chain amino acid sequences for Antibodies A, D, and E and the nucleotide sequences encoding the same, are listed in the section entitled "Amino Acid and Nucleotide Sequences." In addition, the SEQ ID NOs for the light chain, heavy chain, light chain variable region, and heavy chain variable region of Antibodies A, D, and E are shown in Table 1 below.

The antibodies of the present invention, including, but not limited to, Antibodies A, D, and E can be made and purified essentially as follows. An appropriate host cell, such as HEK 293 or CHO, can be either transiently or stably transfected with an expression system for secreting antibodies using an optimal predetermined HC:LC vector ratio or a single vector system encoding both HC (heavy chain) and LC (light chain). Clarified media, into which the antibody has been secreted, may be purified using any of many commonly-used techniques. For example, the medium may be conveniently applied to a Mab Select column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by UV absorbance or SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is typically greater than 95%. The product may be immediately frozen at −70° C. or may be lyophilized.

TABLE 1

| Corresponding SEQ ID | Antibody A (anti-Tim-3 Antibody) | Antibody D (Anti-PD-1 Antibody - S228P IgG4) | Antibody E (Anti-PD-1 Antibody - PAA IgG4 des-Lys) |
|---|---|---|---|
| HCDR1 | 2 | 16 | 16 |
| HCDR2 | 3 | 17 | 17 |
| HCDR3 | 4 | 18 | 18 |
| LCDR1 | 5 | 19 | 19 |
| LCDR2 | 6 | 20 | 20 |
| LCDR3 | 7 | 21 | 21 |
| HCVR | 8 | 22 | 22 |
| LCVR | 9 | 23 | 23 |
| Heavy chain | 10 | 24 | 25 |
| Light chain | 11 | 26 | 26 |
| DNA Heavy Chain | 12 | 27 | 28 |
| DNA Light Chain | 13 | 29 | 29 |

WINN Assay

The antibodies of the present invention can be tested for in vivo immunomodulatory activity with the WINN assay. In the WINN assay, human NSCLC tumor cells NCI-H292 and human immune cells (allogeneic) are mixed and co-implanted into an immunodeficient mouse, and then followed by dosing with an immunomodulatory agent. The ability of the immunomodulatory agent to inhibit or delay tumor formation or support intra-tumroal persistence can be assessed as follows.

On day 0, NSG mice from Jackson Laboratories (7 weeks of age, female, in groups of 8-10 mice) are implanted into the flank subcutaneously with either $2\times10^6$ H292 cells, or a mixture of $2\times10^6$ H292 cells and $1\times10^6$ human PBMCs in HBSS (0.2 ml total volume). Starting on Day 0, mice are treated with an i.p. injection of control human IgG at 10 mg/kg or Antibody A at 1 mg/kg or 10 mg/kg, one time per week for six weeks. Animal well-being and behavior, including grooming and ambulation, are monitored at least twice per week.

Tumor sections from the model can be analyzed for CD3-positive and CD8-positive T cell persistence by measuring the presence of CD3-positive and CD8-positive T cells by staining for CD3 and CD8 and analyzing with the Aperio ScanScope™. The IHC Nuclear Image Analysis macro detects nuclear staining for a target chromogen for the individual cells in those regions that are chosen by the user and quantifies their intensities. Three to five annotations are made from viable tumor area and used in adjusting the parameters until the algorithm results generate consistent cell identification. The macro is then saved and the slides logged in for analysis. The % CD3-positive and CD8-positive cells as a percent of the total number of cells are calculated by the Aperio software.

In experiments performed essentially as described in this WINN assay, by IHC analysis, mice co-implanted with NCI-H292 tumors and PBMCs and dosed with Antibody A at 10 mg/kg results in a significant increase (30%) of human CD3-positive CD8-positive intratumoral T cells as compared to mice co-implanted with NCI-H292 tumors and PBMCs and treated with the control IgG (6.5%) (P=0.03).

Established Human Tumor Xenograft Model in NSG Mice Humanized with Primary Human T Cells The efficacy of the antibodies of the present invention can be tested in the NCI-HCC827 human NSCLC (non-small cell lung cancer) xenograft model to assess the ability to delay or destroy established tumors in the model. On day 0, $1\times10^7$ NCI-HCC827 cells are implanted subcutaneously into the flank of NSG mice (7 weeks of age, female, 8 mice per group). When tumors reach a volume of ~400 $mm^3$ (~days 30-32), the mice are infused (i.v.) with $2.5\times10^6$ previously expanded human T cells. Previously expanded human T cells are generated by isolating human T cells from whole blood and expanding using Dynabeads® Human T-Activator CD3/CD28 for 10 days. Previously expanded human T cells may be cryopreserved for later use. One day after T cell infusion, mice are dosed at 10 mg/kg by weekly (4 total doses) i.p. injection with human IgG or Antibody A. Animal well-being and behavior, including grooming and ambulation are monitored at least twice per week.

Body weight and tumor volume are measured twice a week. Tumor volumes were measured twice per week starting on day 4 post-cell implantation using electronic calipers as described above. Tumor Volume ($mm^3$)=$\pi$/6*Length*Width$^2$. The antitumor efficacy is expressed as T/C ratio in percent and calculated as summarized below: % T/C is calculated by the formula 100 $\Delta T/\Delta C$ if $\Delta T>0$ of the geometric mean values. $\Delta T$=mean tumor volume of the drug-treated group on the final day of the study−mean tumor volume of the drug-treated group on initial day of dosing; $\Delta C$=mean tumor volume of the control group on the final day of the study−mean tumor volume of the control group on initial day of dosing. Additionally, % Regression is calculated using the formula=$100\times\Delta T/T_{initial}$ if $\Delta T<0$. Animals with no measurable tumors are considered as Complete Responders (CR) and tumors with >50% regressions are Partial Responders (PR).

In experiments performed essentially as described above, treatment with Antibody A (anti-human Tim-3) significantly inhibits tumor growth in the humanized NSG mice, compared to treatment with human IgG (Table 2). On day 76, treatment with Antibody A results in a T/C=2%. On day 110, Antibody A treatment results in a 3/8 CR.

TABLE 2

Tumor volume ($mm^3$) in the NCI-HCC827 human NSCLC xenograft model

| | Human IgG Control | | Antibody A | |
|---|---|---|---|---|
| Day | Mean | SEM | Mean | SEM |
| 21 | 152 | 13 | 164 | 85 |
| 28 | 289 | 24 | 309 | 160 |
| 30 | 332 | 28 | 358 | 186 |
| 34 | 388 | 32 | 403 | 209 |
| 36 | 414 | 34 | 505 | 262 |
| 40 | 706 | 59 | 628 | 326 |
| 43 | 752 | 62 | 733 | 380 |
| 47 | 858 | 71 | 763 | 396 |
| 50 | 932 | 77 | 747 | 387 |
| 55 | 982 | 81 | 807 | 418 |
| 57 | 1212 | 100 | 843 | 437 |
| 62 | 1324 | 110 | 553 | 287 |
| 65 | 1524 | 126 | 726 | 376 |
| 69 | 1492 | 124 | 602 | 312 |
| 72 | 1827 | 151 | 539 | 279 |
| 76 | 2030 | 168 | 375 | 196 |
| 79 | | | 375 | 196 |
| 83 | | | 414 | 218 |
| 85 | | | 331 | 175 |
| 90 | | | 192 | 103 |
| 93 | | | 235 | 128 |
| 97 | | | 173 | 95 |
| 100 | | | 118 | 65 |
| 103 | | | 125 | 69 |
| 106 | | | 120 | 67 |
| 110 | | | 131 | 73 |

L55 Assay

The antibodies of the present invention can be tested for in vivo immunomodulatory activity with the L55 assay. In this regard, the efficacy of Antibody A and of the combination of Antibody A and the anti-PD-1 antibody, Antibody D, to enhance T cell responses to allo-antigens can be evaluated using the L55 (non-small cell lung cancer) established xenograft model. L55 cells are cultured in RPMI-1640 media with 10% fetal bovine serum and 1 mM $Na^+$ Pyruvate and L-Glutamine. On day 0, NSG mice from Jackson Laboratories (7 weeks of age, female, in groups of 8 mice) are implanted into the flank subcutaneously with $5\times10^6$ L55 human NSCLC cells in HBSS (0.2 ml total volume). When the tumors reach ~200-300 mm (~day 21-25), the mice are randomized. Human PBMC cells are isolated from whole blood and infused intravenously ($8\times10^6$ PBMC in 0.2 ml PBS per mouse) into L55 tumor-bearing mice on day 28. On the same day, mice are treated with an intraperitoneal injection of human IgG or Antibody A at 10 mg/kg, once weekly for four weeks in total (dosed on d28, d35, d42, d48).

Antibody D treatment at 10 mg/kg starts on day 31 and is administered once weekly for three more weeks (dosed on d31, d38, d45, d48). Animal well-being and behavior, including grooming and ambulation, are monitored at least twice per week. Body weight and tumor volume are measured twice a week. Tumor volumes are measured twice per week starting on day 4, post cell implantation using electronic calipers. Tumor volume is calculated using the formula: Tumor Volume ($mm^3$)=π/6*Length*Width$^2$.

In experiments performed essentially as described in this assay, combination treatment with Antibody A (anti-human Tim-3) and Antibody D (anti-human PD-1) significantly delay tumor growth in the humanized NSG mice, compared to treatment with either Antibody A or Antibody D alone (Table 3).

TABLE 3

| | Human IgG Control | | Antibody A | | Antibody D | | Antibody A + Antibody D | |
|---|---|---|---|---|---|---|---|---|
| Day | Mean | SEM | Mean | SEM | Mean | SEM | Mean | SEM |
| 16 | 113.7 | 3.6 | 109 | 5.5 | 110.7 | 4.6 | 103.9 | 6.3 |
| 24 | 251.6 | 19.7 | 236.9 | 12.1 | 238.9 | 17.5 | 228 | 21.9 |
| 28 | 364.0 | 27.7 | 344.1 | 17.6 | 342.6 | 25.1 | 358.5 | 34.4 |
| 31 | 483.7 | 36.9 | 441.7 | 22.6 | 457.3 | 33.5 | 447 | 42.8 |
| 35 | 480.0 | 36.6 | 491.9 | 25.2 | 538.6 | 39.6 | 388.7 | 37.3 |
| 38 | 545.7 | 41.6 | 582.6 | 29.8 | 655.3 | 48.1 | 492.3 | 47.2 |
| 42 | 657.8 | 50.2 | 651.2 | 33.3 | 607.5 | 44.5 | 391.5 | 37.5 |
| 44 | 916.0 | 69.8 | 756.6 | 38.7 | 896.9 | 65.8 | 520.4 | 49.9 |
| 48 | 1027.5 | 78.3 | 766.8 | 39.3 | 772.6 | 56.7 | 599.6 | 57.5 |
| 50 | 1173.0 | 89.4 | 911 | 46.6 | 943.8 | 69.2 | 720.3 | 69 |
| 55 | 1298.1 | 98.9 | 1170.6 | 59.9 | 1125.8 | 82.6 | 816.6 | 78.3 |
| 58 | | | 1839.9 | 94.2 | 1530.7 | 112.2 | 931.0 | 89.2 |
| 62 | | | | | | | 1019.5 | 97.7 |
| 65 | | | | | | | 1147.7 | 110 |
| 69 | | | | | | | 1272.5 | 122 |

Modified Mixed Lymphocyte Reaction

The function of blocking Tim-3 signals by antibodies of the present invention may be evaluated by measuring the release of cytokines during T cell activation. The levels of certain cytokines, such as IFN-γ, are expected to increase if T cell activation is promoted by treatment with antibodies of the present invention.

$CD14^+$ monocytes are isolated by negative selection from fresh human PBMC obtained from a healthy donor (AllCells) using human monocyte isolation kit II (Miltennyi Biotec). Human monocyte-derived dendritic cells are generated by culturing the $CD14^+$ monocytes in complete RPMI-1640 medium in the presence of 62.5 ng/ml hGM-CSF and 20 ng/ml human IL-4 for 3 days. Fresh human PBMC were isolated from different healthy donor (AllCells). The two types of cells are then mixed in individual wells of a 96-well plate with 100 μl complete AIM-V medium containing 7.5×10$^4$ PBMC cells and 1.5×10$^4$ immature DC per well. 100 μl complete AIM-V medium is added containing 100 nM human IgG1, 100 nM Antibody A, 0.64 nM or 0.32 nM nivolumab, 100 nM Antibody A and 0.64 or 0.32 nM Nivolumab combination in 8 replicates. After incubation for 6 days at 37° C. at 5% $CO_2$, supernatants are harvested and measured for human IFN-γ with an ELISA kit (R&D Systems). An unpaired t-test is used to compare groups.

In experiments performed essentially as described above, the addition of Antibody A or nivolumab increases the secretion of IFN-γ as compared to the addition of human IgG1. The combination of Antibody A with nivolumab significantly increases the secretion of IFN-γ as compared to the addition of nivolumab alone at the dose of 0.32 nM dose (P=0.0013), as illustrated in Table 4 below.

TABLE 4

| | Control IgG (100 nM) | | | Antibody A (100 nM) | | |
|---|---|---|---|---|---|---|
| | Nivolumab | | | | | |
| | 0 nM | 0.32 nM | 0.64 nM | 0 nM | 0.32 nM | 0.64 nM |
| IFN-gamma (pg/ml) | 157.554 ± 79.3 | 180.326 ± 37.3 | 232.656 ± 58.7 | 201.419 ± 120.7 | 310.846 ± 66.1 | 369.109 ± 179.4 |

ELISA Analysis: Antibody A Binds to Recombinant Tim-3

The ability of antibodies of the present invention to bind human Tim-3 can be measured with an ELISA assay. For the Tim-3 binding assay, a 96-well plate (Nunc) is coated with human Tim-3-Fc (R&D Systems) overnight at 4° C. Wells are blocked for 2 h with blocking buffer (PBS containing 3% bovine serum albumin). Wells are washed three times with PBS containing 0.1% Tween-20. Antibody A or control IgG (100 μl) is then added and incubated at room temperature for 1 h. After washing, the plate is incubated with 100 μl of goat anti-human IgG F(ab')2-HRP conjugate (Jackson Immuno Research) at room temperature for 1 h. The plates are washed and then incubated with 100 μl of 3,3',5,5'-tetramethylbenzidine. The absorbance at 450 nm is read on a microplate reader. The half maximal effective concentration (EC50) is calculated using GraphPad Prism 6 software.

In experiments performed essentially as described above, Antibody A binds human Tim-3 with an EC50 of 2.07×10$^{-11}$ M.

Flow Cytometric Analysis: Antibody A Binds to Cell Surface Tim-3

The ability for antibodies of the present invention to bind to cell surface human Tim-3 can be measured with a flow cytometric assay. Tim-3 DO11.10 cells, a human Tim-3 expressing DO11.10 cell line, are used for this assay.

Tim-3 D011.10 cells can be obtained as follows. Full-length Tim-3 gene can be purchased from Origene Technologies, Inc. and cloned into a pLVX-IRES-Neo lentivirus vector from Clonetech Laboraties, Inc. using PCR. Lenti-X™ system from Clonetech Laboraties, Inc. is used to generate high titers of recombinant, replication-incompetent virions. The virions are either used to infect the target cells immediately or are aliquoted and frozen at −80 until use. The murine T cell hybridoma, D011.10 cell line, can be obtained from the National Jewish Health®. The D011.10 cells are cultured and maintained according to a protocol accompanying this cell line. On day 0, DO11.10 cells are counted and spun down to remove culture media. Cell pellets are mixed with virions containing the human TIM-3 gene or vector control and incubated at 37° C. for 24 hours. Polybrene is added when mixing cells and virions until a final concentration of 8 ug/ml is achieved. After 24 hours, DO11.10 cells are pelleted again and resuspended in fresh culture media and incubated at 37° C. for 3 days. Next, the DO11.10 cells are pelleted every 3 days and resuspended in selection media containing 1 mg/ml Geneticin® to select stably transduced cells. Tim-3 expression is monitored by flow cytometry using antibodies obtained from R&D Systems. After 2 to 3 weeks in selection media, the resulting Tim-3 expressing DO11.10 cells are sorted to establish a single cell clone. DO11.10 and Tim-3 DO11.10 cells are added to a 96 well V-bottom plate at $1.\times10^5$ cells per well (100 μl/well) in staining buffer (DPBS containing 3% BSA). Cells are Fc blocked on ice for 1 hour in staining buffer with 30 μg/mL human IgG. Antibody A or control human IgG is labelled with A488 (Molecular Probes®) and 12 point titrations (1:3 serial dilutions) of both antibodies are prepared in staining buffer with a starting concentration of 66.7 nM. Labelled antibodies are added to the cells and incubated for 1 hour at 4° C. in the dark. Cells are washed two times with PBS by spinning for 5 min at 1200 RPM and decanting the supernatant. Live/Dead cell dye 7-AAD (1:1000 in PBS) is added to each well at 3 μl/well and cells are incubated for 15 min on ice. Cells are washed two times with PBS and resuspended in 100 μl DPBS containing 0.5% BSA and analyzed on an Intellictye iQue. All stainings are done in triplicate. Data are analyzed with FlowJo software to identify populations of live cells and determine the median fluorescence intensity of each sample using the AF488 (FL1) detection channel. The individual MFI (i.e. mean fluorescence intensity) values are placed into GraphPad Prism software to generate concentration response curves from which EC50 values are extrapolated.

In experiments performed essentially as described above, Antibody A binds to cellular bound human Tim-3 on Tim-3 D011.10 cells in a dose dependent manner with an EC50 value of 0.09 nM.

Flow Cytometric Analysis: Antibody A Blocks the Interaction of Phosphatidylserine with Human Tim-3

The ability for certain antibodies of the present invention to block phosphatidylserine binding to Tim-3 can be measured by FACS analysis. For this receptor-ligand blocking assay, $1\times10^6$/ml of D011.10 cells are treated with 12 μM camptothecin (Sigma®) for 3 hours at 37° C. to induce apoptosis. FITC-Annexin V (Becton Dickinson®) is used as a positive control to detect the existence of phosphatidylserine. Biotinylated hTIM-3-Fc binds strongly to camptothecin-treated cells but does not bind to non-treated cells. Camptothecin-treated cells are washed with cold PBS and resuspended in binding buffer (Becton Dicknson®) at $1\times10^6$ cells/ml. Fc receptors are blocked by adding 50 μg/ml mouse IgG and rat IgG to the cells and incubating at room temperature for 30 min. 6 point titrations (1:3 serial dilutions) of Antibody A are prepared in binding buffer with a starting concentration of 90 nM and added to 1 ml of cells and cells are then incubated for 60 min at room temperature. hTIM-3-Fc Biotin is then added at 0.05 μg/well to the appropriate samples in a 200 μl volume and incubated for 30 min at room temperature. Cells are then washed twice with binding buffer by centrifugation at 1200 RPM for 5 min. 2.4 μl/well of a streptavidin-FITC (Biolegend®) containing solution (1:10 dilution in DPBS) and 5 μl/well of propidium iodide are added to each well and incubated for 30 min at room temperature in the dark. Cells are washed twice with binding buffer and resuspended in 100 μl of PBS. Samples are read on the IntelliCyt iQue Flow Cytometer and Data were analyzed with FlowJo software. The individual MFI (i.e. mean fluorescence intensity) values are placed into GraphPad Prism software to generate concentration response curves from which IC50 values are extrapolated.

In experiments performed essentially as described above, Antibody A blocks the interaction of human Tim-3 with phosphatidylserine in a dose-dependent manner with an IC50 value of 0.32 nM and as further illustrated in Table 4.

TABLE 4

| | Untreated DO11.10 + hTIM-3-Fc Biotin | Camptothecin-treated DO11.10 + hTIM-3-Fc Biotin Antibody A (nM) | | | | | | |
|---|---|---|---|---|---|---|---|---|
| | 0 | 90 | 30 | 10 | 3.3 | 1.1 | 0.37 | 0 |
| MFI | 1747 | 1815 | 19655 | 32574 | 52885 | 96566 | 197146 | 214044 |

Galectin-9 Blocking Assay: Antibody A Blocks the Interaction of Human Galectin-9 with Human Tim-3

The ability for antibodies of the present invention to block human galectin-9 binding to human Tim-3 can be measured as follows. For this receptor-ligand blocking assay, a 96-well streptavidin-coated MSD plate (Meso Scale Diagnostics) is blocked for 2 hours with 150 μl blocking buffer (PBST containing 5% bovine serum albumin). Wells are washed three times with 200 μl PBS containing 0.2% Tween-20. Recombinant human galectin-9 (R&D Systems) is biotinylated using EZ-Link™ biotin (Thermo Scientific™) and then 25 μl of 0.21 μg/ml of the human recombinant galectin-9-biotin is then added and incubated at room temperature for 2 hours. Plates are washed three times with PBS containing 0.2% Tween-20. Human Tim-3-Fc protein (R&D Systems) is ruthinylated using sulfo-tag NETS-ester reagent (Meso Scale Discovery®) and a small aliquot is stored at −80 until use. Antibodies are serially diluted (starting at 13.5 μg/ml) and 50 μl of each antibody combined with 50 μl of diluted hTim-3-Fc-ruth at 0.05 μg/ml and incubated for 1 hour at room temperature. 50 μl of each combination is then added to the plate and incubated for 1.5 hours at room temperature. Plates are washed three times with PBS containing 0.2% Tween-20. 150 μl of 1× read buffer (Meso Scale Diagnostics) is then added to each well of the plate and the plate is read on a Sector Imager 2400 (Meso Scale Diagnostics).

In experiments performed essentially as described above, Antibody A blocks the interaction of human Tim-3 with human galectin-9 with an IC50 value of 5.6 nM as compared to control a polyclonal anti-human Tim-3 antibody (R&D Systems) with an IC50 value of 7.8 nM. However, The polyclonal anti-human Tim-3 antibody can block up to 100% human Tim-3's interactions with human galectin-9 while Antibody A only achieve partial blockage in this assay.

CEACAM-1 Blocking Assay: Antibody A does not Block the Interaction of Human CEACAM1 with Human Tim-3

The ability for antibodies of the present invention to block human CEACAM1 binding to human Tim-3 can be measured as follows. For this receptor-ligand blocking assay, a 96-well Immulon 4HBX plate (Thermo Scientific) is coated with 100 μl/well of 1 ug/ml human Tim-3-Fc at 4° C. The plate is washed three times with PBS containing 0.2% Tween-20 and blocked with 200 μl/well of PBS with 3% BSA for 1 hour at room temperature. Blocking buffer is then removed and 50 μl of titrated Abs (including polyclonal anti-human Tim-3, R&D Systems, Antibody A, and control human IgG), starting at 600 nM are added to the plate and incubated for 1 hour at room temperature. 50 μl of 20 μg/ml of CEACAM1 (BIOTANG) is then added directly to the wells and incubated for 1 hour at room temperature (final concentration of antibody is 300 nM and of CEACAM1 is 10 μg/ml). The plate is washed three times with PBS containing 0.2% Tween-20 and 100 μl of 0.2 μg/ml of biotinylated human CEACAM1 antibody (R&D Systems) is added and then incubated for 1 hour at room temperature. The plate is washed three times with PBS containing 0.2% Tween-20 and then 100 μl of streptavidin peroxidase (Jackson ImmunoResearch Laboratories) is added and then incubated for 1 hour at room temperature. The plate is washed six times with PBS containing 0.2% Tween-20 and developed using 100 μl/well of a 1:1 TMB substrate solution A and B (KPL) for 10 min at room temperature. The reaction is then stopped with 100 μl/well of 0.1N H2504 and the plate is read on a SpectraMax® plate reader at 450 nm.

In experiments performed essentially as described above, Antibody A does not significantly block the binding of CEACAM1 to human Tim-3, as illustrated in Table 5 below.

TABLE 5

| | Concentration of Antibody (nM) | | | | | | | | | |
|---|---|---|---|---|---|---|---|---|---|---|
| | 0.015 | 0.046 | 0.137 | 0.41 | 1.24 | 3.71 | 11.1 | 33.3 | 100 | 300 |
| Human IgG Control (O.D.) | 2.05 | 2.02 | 2.13 | 2.03 | 2.04 | 2.03 | 2.05 | 2.07 | 2.12 | 2.08 |
| Polyclonal Anti-Tim-3 (O.D.) | 1.96 | 1.88 | 1.89 | 1.88 | 1.85 | 1.80 | 1.51 | 1.16 | 0.99 | 0.99 |
| Antibody A (O.D.) | 1.87 | 1.88 | 1.87 | 1.82 | 1.80 | 1.78 | 1.79 | 1.79 | 1.73 | 1.74 |

Epitope

A Fab for Antibody A is generated by enzymatically clipping Antibody A with immobilized (agarose resin) papain (ThermoFisher Scientific) followed by a standard ProA column (GE Healthcare Life Sciences) purification to pull out the free, soluble Fc and the unclipped IgG. Flow through containing the Fab is collected to concentrate and buffer exchange. The hTim-3-IgV-FLAG is purified from the 293HEK supernatant with a standard anti-FLAG resin (Sigma-Aldrich) protocol. The hTim-3-IgV domain represents amino acid residues S22 to K130 of human Tim-3 (SEQ ID: 1). Flow through is rerun in the resin column multiple times. After each run, SDS-PAGE (NuPAGE Novex 4-12% Bis-Tris Gels; Invitrogen) and HPLC (TSK-gel G3000 SW XL (Dimensions: 7.8 mm, ID 30 CM, 5 μM; TOSHO BioSCIENCE) is utilized to determine quality of the hTim-3-FLAG protein. Proteins of the best rounds are combined together to generate the final batch.

hTim-3-IgV-FLAG, at 2.17 mg/mL in TBS buffer pH 7.2, and Antibody A-Fab, at 6.79 mg/mL, are combined in a 1:1 molar ratio and the complex is isolated via size exclusion chromatography with a final concentration of 6.9 mg/mL in 20 mM hepes pH 7.4 and 150 mM sodium chloride. The Tim-3-anti-Tim-3 complex is screened in five Qiagen grid screens at both 8° C. and 21° C. using the sitting drop vapor diffusion method. Drops are set up using an Art Robbins Phoenix liquid handling robot which dispenses 0.3 μL crystallization solution on top of 0.3 μL protein. 100-200 μm intergrown prisms are obtained at 21° C. in 20% PEG 3350 and 0.2 M lithium chloride. Crystals are harvested and cryoprotected in a solution made of the crystallization condition supplemented with 20% ethylene glycol prior to flash freezing in liquid nitrogen. A dataset is collected at Argonne National Laboratory diffracting to 2.2 Å in space group P21 with cell parameters a=74.62 Å, b=57.85 Å, and c=74.71 Å.

The structure of the Antibody A-Fab in complex with human Tim-3 is determined by Molecular Replacement using the program Phaser. High resolution and publicly available Fab structures and the published structure of murine Tim-3 can be used as Molecular Replacement models. The structure is refined using the program Refmac and the model rebuilt using the program COOT. Final refinement R-factors are Rwork=20.2%, Rfree=23.4%. There are no Ramachandran violators, and 96.4% of the residues are in the favored region of the Ramachandran plot. There is density indicating glycosylation at Asn99 of Tim-3 (SEQ ID NO:1).

A BIACORE T200™ system is utilized to determine the binding kinetics of hTim-3-IgV-FLAG to the captured Antibody A-Fab. In HBS-EP as a running buffer, 1:1 binding of this complex at 25° C. has a $k_{on}$ of 3.62E+05 1/Ms, $k_{off}$ of 2.86E-03 1/s, and a $K_D$ of 7.92E-09 M.

In experiments performed essentially as described in this assay, Antibody A-Fab/hTim-3 complex is resolved and the epitope/paratope is illustrated in Table 6 below. Table 6 below lists the residues on Antibody A-Fab that are within 6 Å of the listed residues on hTim-3 (SEQ ID NO:1). The heavy chain of the Antibody A-Fab has 62 contacts (cutoff 6 Å) with hTim-3 while the light chain has 34 contacts (cutoff 6 Å).

TABLE 6

| Tim-3 (Epitope) | Antibody A Heavy Chain (Paratope) | Antibody A Light Chain (Paratope) |
|---|---|---|
| P50 | S54 | — |
| K55 | — | Y32 |
| G56 | — | Y32 |
| A57 | — | Y30, Y32, N92 |
| C58 | — | Y32, A91, N92, S93 |
| P59 | Y99, T102 | Y32, A91, N92, S93 |
| V60 | Y59, Y99, T102 | Y32, Q89, Q90, A91, N92, S93, F94, P95, P96 |

TABLE 6-continued

| Tim-3 (Epitope) | Antibody A Heavy Chain (Paratope) | Antibody A Light Chain (Paratope) |
|---|---|---|
| F61 | Y33, S35, W47, A50, Y59, Y99, A100, T102, F104 | A91, F94, P96 |
| E62 | S31, Y33, Y59, Y99, R101 | — |
| C63 | Y99, R101, T102 | Y32 |
| G64 | T102 | Y32 |
| N65 | T102 | N31, Y32, A50 |
| E72 | S54 | — |
| I107 | — | T30 |
| R111 | Y33, Y59 | — |
| Q113 | Y33, S52, G53, S54, G55, G56, S57, Y59 | — |
| I114 | G56, S57 | — |
| P115 | G56, S57 | — |
| G116 | G56, S57, T58, Y59 | — |
| I117 | G56, S57, T58, Y59, Y60, K65 | — |
| M118 | S57, T58, Y59, Y60, A61, D62, K65 | F94 |
| N119 | T58, Y59 | — |
| D120 | Y33, S57, Y59 | — |
| K122 | — | N92, F94 |

Kinetics/Affinity Study for Antibody A

A BIACORE T100™ system instrument can be used to measure the kinetics of human Tim-3-IgV-Fc single arm antigen (SAG) binding to captured Antibody A. Human Fab Binder surfaces are prepared by amine-coupling Human Fab Binder (GE Healthcare) to a BIACORE CM5 system™ sensor chip surface. Test antibodies are captured by the chip using HBS-EP buffer (GE Healthcare) as the running buffer. Tim-3 SAG is diluted into running buffer starting at 30 nM with a dilution factor of 3 to give concentrations of 0.04, 0.12, 0.37, 1.11, 3.33, 10 and 30 nM. Diluted Tim-3 SAG analyte or buffer is injected at 30 μl/min for 180 seconds and the complex dissociation is monitored for 1200 seconds. The binding surface is regenerated with injection of 10 mM Glycine-HCl pH 2.1 at 30 μl/min, 30 seconds of two injections for five lower concentrations, and two injections at 60 seconds for two higher concentrations between each analyte binding cycle. Experimental data for a given antigen/Ab interaction are fit using a 1:1 Langmuir with mass transport Model.

In experiments performed essentially as described above, Antibody A binds to human Tim-3 with the kinetics and affinity constants illustrated in Table 7.

TABLE 7

| Antibody | $K_{on}$ (1/Ms) | $K_{off}$ (1/s) | $K_D$ (M) | $R_{max}$ | Chi$^2$ |
|---|---|---|---|---|---|
| Antibody A | 2.33E+06 | 9.27E−04 | 3.98E−10 | 17.09 | 0.319 |

Surface Plasmon Resonance (SPR)

Immobilization of human PD-1-Fc (R&D Systems) as a ligand on to sensor chip surface is performed at 25° C. Anti-Antibodies of the present invention are used as analyte, and injected over the human PD-1-Fc immobilized sensor chip surface. All sample analytes are run in 3-fold series dilutions from their starting concentration (90 nM), 8 total dilutions with one duplicate at a middle concentration and a zero. The analysis is performed at 37° C. The contact time for each sample is 180 sec at 30 μl/min. The dissociation time: 300 seconds for 5 lower concentrations and 1200 (Fab), or 2400 (T=0) or 3000 (4 weeks 4° C., 25° C., 40° C.) seconds for 3 higher concentrations. The immobilized surface is regenerated for 6-8 seconds with 0.4% SDS at 30 μl/min, and then stabilized for 5 seconds. Binding kinetics are analyzed using the BIACORE T200™ system Evaluation software (Version 3.0). Data are referenced to a blank flow cell, and the data are fit to a 1:1 binding model.

In experiments performed essentially as described in this assay, Antibody D binds with a $K_D$ to human PD-1 of 102 μM, nivolumab with a $K_D$ of 246 μM, and pembrolizumab with a $K_D$ of 181 μM. As shown in Table 8, Antibody D maintained binding activity at 4 weeks under elevated temperature conditions.

TABLE 8

| Binding by SPR of Antibody D at extended times and temperatures | | | |
|---|---|---|---|
| Binding to human PD-1-Fc | Kon (1/Ms) | Koff (1/s) | $K_D$ (pM) |
| Antibody D | 2.86E+05 | 2.98E−05 | 104 |
| Antibody D, 4 weeks 4° C. | 3.77E+05 | 3.86E−05 | 103 |
| Antibody D, 4 weeks 25° C. | 3.54E+05 | 3.60E−05 | 102 |
| Antibody D, 4 weeks 40° C. | 3.58E+05 | 4.22E−05 | 118 |

Blocking of Human PD-1 Interaction with PD-L1 and PD-L2.

For the receptor-ligand blocking assay, varying amounts of the indicated anti-PD-1 antibody or control IgG are mixed with a fixed amount of biotinylated PD-1-Fc fusion protein (100 ng/mL) and incubated at room temperature for 1 hour. The mixture is transferred to 96-well plates pre-coated with PD-L1-Fc (100 ng/well) or PD-L2-Fc (100 ng/well) and then incubated at room temperature for an additional 1 hour. Plates are washed and streptavidin HRP conjugate is added. Plates are read at an absorbance at 450 nm. IC50 represents the antibody concentration required for 50% inhibition of PD-1 binding to PD-L1 or binding to PD-L2.

In experiments performed essentially as described, Antibody D blocks the interaction of PD-1 with PD-L1 with an IC50 of 0.30 nM, and the interaction of PD-1 with PD-L2 with an IC50 of 0.34 nM.

Binding to Human PD-1 on CHO Cells

The binding of an antibody of the present invention to human PD-1 may be measured by flow cytometry.

CHO cells (0.2×10$^6$) are incubated with antibody from 200 nM titrated 19× by a factor of 2 to the lowest concentration of 3.185 pM for 30 min in PBS 1% BSA on ice. Cells are then washed 3×, and are incubated with a secondary antibody (PE-labelled, at final concentration of 5 μg/ml) in PBS 1% BSA for 30 min on ice (protected from light). Cells are washed 3× and analyzed via flow cytometry. Flow cytometry is performed on an Accuri C6 system (BD Biosciences) and MFIs are calculated on the C6 software. EC50s are calculated on Graphpad software.

In experiments performed essentially as described in this assay, Antibody G binds PD-1 in a dose-dependent manner, with an EC50 value (n=1) of 1.756 nM and pembrolizumab binds PD-1 with an EC50 value (n=1) of 1.429 nM. Antibody D binds PD-1 in a dose-dependent manner, with an EC50 value (n=1) of 0.9784 nM, pembrolizumab with an EC50 value (n=1) of 0.9510 nM, and nivolumab with an EC50 value (n=1) of 0.9675 nM. Antibody D binds with a similar EC50 to human PD-1 as nivolumab and pembrolizumab under these conditions.

Blocking of Human PD-1 to PD-L2 in CHO Cells.

The ability of an anti-human PD-1 antibody of the present invention to block binding of human PD-1 to PD-L1 and PD-L2 can be measured by flow cytometry.

CHO cells ($0.2\times10^6$) are incubated with the experimental antibody 100 nM for 30 min in PBS 1% BSA on ice. Cells are then washed 3×, and are incubated with PD-L2 linked with NHS-Fluorescein (Promega) in PBS 1% BSA for 30 min on ice (protected from light). Cells are washed 3× and analyzed via flow cytometry. Flow cytometry is performed on an Accuri C6 system (BD Biosciences) and mean fluorescence intensity (MFI) is calculated on the C6 software.

In experiments performed essentially as described in this assay, Antibody D, in IgG1 format and expressed in yeast, blocked human PD-L2-FITC binding, resulting in an MFI of 24,697.7 as compared to control IgG which resulted in an MFI of 182,959.1. Pembrolizumab and nivolumab resulted in less blocking of PD-L2 binding to PD-1 than Antibody D with an MFI of 46,245.9.

TABLE 7

Blocking of human PD-1 on CHO cells

| Test Sample | MFI (PD-L2-FITC) |
|---|---|
| Cells only | 33,449.7 |
| No IgG | 199,716.0 |
| IgG Control | 182,959.1 |
| Nivolumab | 54,509.8 |
| Pembrolizumab | 46,245.9 |
| Antibody D in IgG1 format | 24,697.7 |

Amino Acid and Nucleotide Sequences

SEQ ID NO: 1 (human Tim-3) (*Homo Sapiens*)
MFSHLPFDCVLLLLLLLLLTRSSEVEYRAEVGQNAYLPCFYTPAAPGNLVP
VCWGKGACPVFECGNVVLRTDERDVNYWTSRYWLNGDFRKGDVSLTIENV
TLADSGIYCCRIQIPGIMNDEKFNLKLVIK SEQ ID NO: 2 (HCDR1 of Antibody A) (Artificial Sequence)
AASGFTFSSYYMS SEQ ID NO: 3 (HCDR2 of Antibody A) (Artificial Sequence)
AISGSGGSTYYADSVKG SEQ ID NO: 4 (HCDR3 of Antibody A) (Artificial Sequence)
ARYARTAFDL SEQ ID NO: 5 (LCDR1 of Antibody A) (Artificial Sequence)
QASQDIYNYLN SEQ ID NO: 6( LCDR2 of Antibody A) (Artificial Sequence)
YAASSLQS SEQ ID NO: 7 (LCDR3 of Antibody A) (Artificial Sequence)
QQANSFPPT SEQ ID NO: 8 (HCVR of Antibody A) (Artificial Sequence)
EVQLLESGGGLVQPGGSLRLSCAASGFTFSSYYMSWVRQAPGKGLEWVSA
ISGSGGSTYYADSVKGRFTISRDNSKNTLYLQMNSLRAEDTAVYYCARYA
RTAFDLWGQGTLVTVSS SEQ ID NO: 9 (LCVR of Antibody A) (Artificial Sequence)
DIVMTQSPSSLSASVGDGVTITCQASQDIYNYLNWYQQKPGKAPKLLIYA
ASSLQSGVPSRFSGSGSGTDFTLTISSLQPEDFATYYCQQANSEPPTEGQ
GTKLEIK -continued Amino Acid and Nucleotide Sequences SEQ ID NO: 10 (HC of Antibody A) (Artificial Sequence)
EVQLLESGGGLVQPGGSLRLSCAASGFTFSSYYMSWVRQAPGKGLEWVSA
ISGSGGSTYYADSVKGRFTISRDNSKNTLYLQMNSLRAEDTAVYYCARYA
RTAFDLWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPEAEGAPSVFLEPPKPKDT
LMISRTPEVTCVVVDVSHEDPEVKFNWYVDGVEVHNAKTKPREEQYNSTY
RVVSVLTVLHQDWLNGKEYKCKVSNKALPSSIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK SEQ ID NO: 11 (LC of Antibody A) (Artificial Sequence)
DIVMTQSPSSLSASVGDGVTITCQASQDIYNYLNWYQQKPGKAPKLLIYA
ASSLQSGVPSRFSGSGSGTDFTLTISSLQPEDFATYYCQQANSEPPTEGQ
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC SEQ ID NO: 12 (DNA of HC of Antibody A) (Artificial Sequence)
GAGGTGCAGCTGTTGGAGTCTGGCGGAGGGCTGGTGCAGCCGGGAGGCAG
CCTCAGGCTGAGCTGCGCTGCGAGCGGGTTTACTTTCTCGTCGTACTATA
TGTCGTGGGTGAGACAAGCACCAGGTAAAGGACTTGAGTGGGTGTCCGCT
ATCTCAGGCAGCGGAGGATCCACCTACTACGCGGATTCAGTCAAGGGAAG
ATTCACTATCTCGCGCGACAATTCCAAGAACACCCTGTACCTCCAGATGA
ACTCGCTGCGGGCAGAAGATACGGCCGTGTACTACTGTGCCCGCTACGCC
CGGACCGCCTTCGACTTGTGGGGTCAGGGAACCCTGGTCACTGTCTCCTC
AGCTAGCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCACTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAGAGTTGAGCC
CAAATCTTGTGACAAAACTCACACATGCCCACCGTGCCCAGCACCTGAAG
CCGAGGGGGCACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTATGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAAGACTGGCTGAATGGCAA
GGAGTACAAGTGCAAGGTCTCCAACAAAGCCCTCCCATCCTCCATCGAGA
AAACCATCTCCAAAGCCAAAGGGCAGCCCCGAGAACCACAGGTGTACACC
CTGCCCCCATCCCGGGAGGAGATGACCAAGAACCAAGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTATTCCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGCAAA SEQ ID NO: 13 (DNA of LC of Antibody A) (Artificial Sequence)
GACATCGTGATGACTCAAAGCCCTTCAAGCCTCTCGGCGTCAGTCGGTGA
TGGCGTGACCATTACCTGTCAAGCATCCCAAGACATCTACAACTACTTGA
ATTGGTACCAGCAGAAGCCAGGGAAAGCCCCGAAGCTGCTGATCTACGCC
GCCTCCTCACTTCAGAGCGGAGTGCCATCCCGCTTTTCCGGATCGGGGAG
CGGAACGGATTTCACTCTGACCATCTCGTCGCTGCAACCGGAGGACTTCG
CGACTTACTATTGCCAGCAGGCTAACTCGTTCCCGCCCACTTTCGGACAG
GGCACCAAGCTCGAAATCAAACGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT SEQ ID NO: 14 (Human CEACAM1) (*Homo Sapiens*)
MGHLSAPLHRVRVPWQGLLLTASLLTFWNPPTTAQLTTESMPFNVAEGKE
VLLLVHNLPQQLFGYSWYKGERVDGNRQIVGYAIGTQQATPGPANSGRET
IYPNASLLIQNVTQNDTGFYTLQVIKSDLVNEEATGQFHVYPELPKPSIS
SNNSNPVEDKDAVAFTCEPETQDTTYLWWINNQSLPVSPRLQLSNGNRTL
TLLSVTRNDTGPYECEIQNPVSANRSDPVTLNVTYGPDTPTISPSDTYYR
PGANLSLSCYAASNPPAQYSWLINGTFQQSTQELFIPNITVNNSGSYTCH
ANNSVTGCNRTTVKTIIVTELSPVVAKPQIKASKTTVTGDKDSVNLTCST
NDTGISIRWFFKNQSLPSSERMKLSQGNTTLSINPVKREDAGTYWCEVFN
PISKNQSDPIMLNVNYNALPQENGLSPGAIAGIVIGVVALVALIAVALAC -continued

| Amino Acid and Nucleotide Sequences |
|---|
| FLHFGKTGRASDQRDLTEHKPSVSNHTQDHSNDPPNKMNEVTYSTLNFEA QQPTQPTSASPSLTATEIIYSEVKKQ |
| SEQ ID NO: 15 (Human Galectin-9) (*Homo Sapiens*)<br>MAFSGSQAPYLSPAVPFSGTIQGGLQDGLQITVNGTVLSSSGTRFAVNFQ TGFSGNDIAFHFNPRFEDGGYVVCNTRQNGSWGPEERKTHMPFQKGMPFD LCFLVQSSDFKVMVNGILFVQYFHRVPFHRVDTISVNGSVQLSYISFQPP GVWPANPAPITQTVIHTVQSAPGQMFSTPAIPPMMYPHPAYPMPFITTIL LGGYPSKSILLSGTVLPSAQRFHINLCSGNHIAFHLNPRFDENAVVRNTQ IDNSWGSEERSLPRKMPFVRGQSFSVWILCEAHCLKVAVDGQHLFEYYHR LRNLPTINRLEVGGDIQLTHVQT |
| SEQ ID NO: 16 (HCDR1 of Antibody D and Antibody E) (Artificial Sequence)<br>KASGGTFSSYAIS |
| SEQ ID NO: 17 (HCDR2 of Antibody D and Antibody E) (Artificial Sequence)<br>LIIPMFDTAGYAQKFQG |
| SEQ ID NO: 18 (HCDR3 of Antibody D and Antibody E) (Artificial Sequence)<br>ARAEHSSTGTFDY |
| SEQ ID NO: 19 (LCDR1 of Antibody D and Antibody E) (Artificial Sequence)<br>RASQGISSWLA |
| SEQ ID NO: 20 (LCDR2 of Antibody D and Antibody E) (Artificial Sequence)<br>SAASSLQS |
| SEQ ID NO: 21 (LCDR3 of Antibody D and Antibody E) (Artificial Sequence)<br>QQANHLPFT |
| SEQ ID NO: 22 (HCVR of Antibody D and Antibody E) (Artificial Sequence)<br>QVQLVQSGAEVKKPGSSVKVSCKASGGTFSSYAISWVRQAPGQGLEWMGL IIPMFDTAGYAQKFQGRVAITVDESTSTAYMELSSLRSEDTAVYYCARAE HSSTGTFDYWGQGTLVTVSS |
| SEQ ID NO: 23 (LCVR of Antibody D and Antibody E) (Artificial Sequence)<br>DIQMTQSPSSVSASVGDRVTITCRASQGISSWLAWYQQKPGKAPKLLISA GASSLQSVPSRFSGSGSGTDFTLTISSLQPEDFATYYCQQANHLPFTFGG GTKVEIK |
| SEQ ID NO: 24 (HC of Antibody D - S228P IgG4) (Artificial Sequence)<br>QVQLVQSGAEVKKPGSSVKVSCKASGGTFSSYAISWVRQAPGQGLEWMGL IIPMFDTAGYAQKFQGRVAITVDESTSTAYMELSSLRSEDTAVYYCARAE HSSTGTFDYWGQGTLVTVSSASTKGPSVFPLAPCSRSTSESTAALGCLVK DYFPEPVTVSWNSGALTSGVHTFPAVLQSSGLYSLSSVVTVPSSSLGTKT YTCNVDHKPSNTKVDKRVESKYGPPCPPCPAPEFLGGPSVFLFPPKPKDT LMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| SEQ ID NO: 25 (HC of Antibody E - PAA IgG4 des-Lys) (Artificial Sequence)<br>QVQLVQSGAEVKKPGSSVKVSCKASGGTFSSYAISWVRQAPGQGLEWMGL IIPMFDTAGYAQKFQGRVAITVDESTSTAYMELSSLRSEDTAVYYCARAE HSSTGTFDYWGQGTLVTVSSASTKGPSVFPLAPCSRSTSESTAALGCLVK DYFPEPVTVSWNSGALTSGVHTFPAVLQSSGLYSLSSVVTVPSSSLGTKT YTCNVDHKPSNTKVDKRVESKYGPPCPPCPAPEAAGGPSVFLFPPKPKDT LMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYT LPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLG |
| SEQ ID NO: 26 (LC of Antibody D and Antibody E) (Artificial Sequence)<br>DIQMTQSPSSVSASVGDRVTITCRASQGISSWLAWYQQKPGKAPKLLISA ASSLQSGVPSRFSGSGSGTDFTLTISSLQPEDFATYYCQQANHLPFTFGG GTKVEIKRTVAAPSVFIFPPSDEQLKSGTASVVCLLNNFYPREAKVQWKV |

-continued

| Amino Acid and Nucleotide Sequences |
|---|
| DNALQSGNSQESVTEQDSKDSTYSLSSTLTLSKADYEKHKVYACEVTHQG LSSPVTKSFNRGEC |
| SEQ ID NO: 27 (DNA of HC of Antibody D - S228P IgG4) (Artificial Sequence)<br>CAAGTGCAGCTGGTGCAGTCCGGCGCTGAGGTGAAAAAACCCGGATCCTC CGTCAAGGTGTCCTGTAAAGCCAGCGGCGGCACATTCAGCAGCTACGCCA TCTCCTGGGTGAGGCAAGCTCCTGGACAGGGCCTGGAATGGATGGGCCTG ATCATCCCCATGTTCGACACCGCCGGCTACGCTCAGAAATTCCAGGGCCG GGTCGCCATTACAGTGGATGAGAGCACCAGCACAGCCTACATGGAGCTCA GCTCCCTGAGGAGCGAAGATACCGCCGTCTACTATTGTGCCCGGGCTGAG CATAGCAGCACCGGCACCTTCGACTATTGGGGCCAGGGAACCCTGGTCAC AGTGAGCTCCGCTTCCACAAAAGGCCCCAGCGTGTTTCCCCTGGCCCCTT GTAGCAGGTCCACCTCCGAAAGCACAGCCGCTCTGGGCTGCCTGGTCAAG GATTACTTCCCCGAGCCCGTGACCGTGTCCTGGAATAGCGGCGCTCTCAC ATCCGGAGTGCATACCTTTCCTGCCGTGCTCCAGTCCTCCGGCCTGTACT CCCTGAGCTCCGTGGTGACCGTCCCTTCCAGCTCCCTGGGCACCAAGACC TATACCTGTAACGTGGACCACAAGCCCTCCAATACCAAGGTGGATAAGCG GGTCGAGTCCAAGTACGGACCCCCTTGCCCTCCTTGTCCTGCTCCTGAAT TCCTCGGCGGACCTAGCGTCTTTCTCTTCCCCCCCAAGCCCAAGGATACC CTGATGATCTCCAGGACCCCCGAGGTGACATGCGTCGTGGTCGATGTGTC CCAGGAGGATCCTGAAGTGCAGTTCAACTGGTACGTGGACGGCGTCGAAG TGCATAACGCCAAGACCAAGCCCAGGGAGGAGCAGTTCAACTCCACCTAT CGGGTGGTGAGCGTGCTGACCGTGCTGCATCAGGACTGGCTCAACGGCAA AGAGTACAAGTGCAAGGTCTCCAACAAGGGACTCCCCTCCAGCATCGAGA AGACCATTAGCAAGGCCAAAGGCCAACCCAGGGAGCCTCAGGTATATACG CTGCCCCCCAGCCAGGAGGAGATGACCAAAAACCAGGTCAGCCTCACCTG TCTGGTCAAGGGCTTCTACCCTAGCGACATTGCTGTCGAGTGGGAGAGCA ACGGCCAGCCCGAGAACAACTATAAAACCACCCCCCCTGTCCTGGACTCC GACGGATCCTTCTTCCTGTACTCCAGGCTGACAGTCGACAAGTCCCGGTG GCAAGAGGGAAACGTCTTCTCCTGCTCCGTGATGCACGAAGCTCTCCACA ACCACTACACCCAGAAGAGCCTCAGCCTGTCCCTGGGCAAATGATGA |
| SEQ ID NO: 28 (DNA of HC of Antibody E - PAA IgG4 des-Lys) (Artificial Sequence)<br>CAGGTGCAGCTGGTCCAGTCAGGGGCTGAAGTGAAGAAGCCCGGCAGCTC CGTGAAGGTGTCTTGCAAGGCCAGCGGCGGAACATTCTCCAGTTACGCCA TCTCTTGGGTGCGGCAGGCTCCAGGCCAGGGCCTGGAGTGGATGGGCCTG ATCATCCCCATGTTCGACACCGCCGGGTATGCCCAGAAGTTTCAGGGCAG AGTGGCAATCACAGTGGACGAGAGCACCTCCACAGCCTACATGGAGCTGT CTAGCCTGAGATCCGAGGATACCGCCGTGTATTATTGTGCCCGGGCCGAA CACAGCTCTACAGGGACTTTCGACTACTGGGGCCAGGGCACCCTGGTGAC AGTGTCCTCTGCTAGCACCAAGGGCCCATCGGTCTTCCCGCTCGCGCCCT GCTCCAGGAGCACCTCCGAGAGCACAGCCGCCCTGGGCTGCCTGGTCAAG GACTACTTCCCCGAACCGGTGACGGTGTCGTGGAACTCAGGCGCCCTGAC CAGCGGCGTGCACACCTTCCCGGCTGTCCTACAGTCCTCAGGACTCTACT CCCTCAGCAGCGTGGTGACCGTGCCCTCCAGCAGCTTGGGCACGAAGACC TACACCTGCAACGTAGATCACAAGCCCAGCAACACCAAGGTGGACAAGAG AGTTGAGTCCAAATATGGTCCCCCATGCCCACCCTGCCCAGCACCTGAGG CCGCCGGGGGACCATCAGTCTTCCTGTTCCCCCCAAAACCCAAGGACACT CTCATGATCTCCCGGACCCCTGAGGTCACGTGCGTGGTGGTGGACGTGAG CCAGGAAGACCCCGAGGTCCAGTTCAACTGGTATGTTGATGGCGTGGAGG TGCATAATGCCAAGACAAAGCCGCGGGAGGAGCAGTTCAACAGCACGTAC CGTGTGGTCAGCGTCCTCACCGTCCTGCACCAGGACTGGCTGAACGGCAA GGAGTACAAGTGCAAGGTCTCCAACAAAGGCCTCCCGTCCTCCATCGAGA AAACCATCTCCAAAGCCAAAGGGCAGCCCCGAGAGCCACAGGTGTACACC CTGCCCCCATCCCAAGAAGAAATGACCAAAAACCAAGTCAGCCTGACCTG CCTGGTCAAAGGCTTCTACCCCAGCGACATCGCCGTGGAGTGGGAAAGCA ATGGGCAGCCGGAGAACAACTACAAGACCACGCCTCCCGTGCTGGACTCC GACGGCTCCTTCTTCCTCTACTCCCGTCTAACCGTGGACAAGAGCAGGTG GCAGGAGGGGAATGTCTTCTCATGCTCCGTGATGCATGAGGCTCTGCACA ACCACTACACACAGAAGAGCCTCTCCCTGTCTCTGGGT |
| SEQ ID NO: 29 (DNA of LC of Antibody D and Antibody E) (Artificial Sequence)<br>GACATCCAGATGACACAGTCCCCTAGCTCCGTGTCCGCTTCCGTGGGAGA CAGGGTGACAATCACATGCAGGGCTTCCCAGGGCATCAGCAGCTGGCTGG CTTGGTATCAGCAGAAGCCCGGCAAGGCCCCCAAGCTGCTGATCAGCGCT GCTAGCTCCCTGCAGTCCGGAGTGCCTTCCAGGTTCTCCGGCTCCGGAAG CGGCACCGACTTCACCCTGACCATCTCCAGCCTGCAGCCCGAGGACTTCG CCACCTACTACTGCCAACAGGCCAACCACCTGCCCTTCACCTTCGGCGGC GGCACCAAGGTGGAGATCAAGAGGACCGTGGCCGCCCCCTCCGTGTTCAT CTTTCCCCCCAGCGACGAGCAGCTGAAGAGCGGCACCGCCTCCGTGGTGT GCCTGCTGAACAACTTCTATCCCCGGGAGGCCAAGGTGCAGTGGAAGGTC GACAATGCCCTGCAGAGCGGCAACTCCCAGGAGAGCGTGACCGAGCAGGA |

-continued

| Amino Acid and Nucleotide Sequences |
|---|
| CAGCAAGGACTCCACCTACTCCCTGAGCTCCACCCTGACACTGTCCAAGG<br>CCGACTACGAGAAGCACAAGGTGTACGCCTGCGAGGTGACACACCAGGGC<br>CTGAGCTCCCCCGTGACCAAGTCCTTCAACAGGGGCGAGTGCTGATGA |
| SEQ ID NO: 30 (Nivolumab Heavy Chain) (Artificial Sequence)<br>QVQLVESGGGVVQPGRSLRLDCKASGITFSNSGMEIWVRQAPGKGLEWVA<br>VIWYDGSKRYYADSVKGRFTISRDNSKNTLFLQMNSLRAEDTAVYYCATN<br>DDYWGQGTLVTVSSASTKGPSVFPLAPCSRSTSESTAALGCLVKDYFPEP<br>VTVSWNSGALTSGVHTFPAVLQSSGLYSLSSVVTVPSSSLGTKTYTCNVD<br>HKPSNTKVDKRVESKYGPPCPPCPAPEFLGGPSVFLFPPKPKDTLMISRT<br>PEVTCVVVDVSQEDPEVQFNWYVDGVEVHNAKTKPREEQFNSTYRVVSVL<br>TVLHQDWLNGKEYKCKVSNKGLPSSIEKTISKAKGQPREPQVYTLPPSQE<br>EMTKNQVSLTCLVKGFYPSDIAVEWESNGQPENNYKTTPPVLDSDGSFFL<br>YSRLTVDKSRWQEGNVFSCSVMHEALHNHYTQKSLSLSLGK |
| SEQ ID NO: 31 (Nivolumab Light Chain) (Artificial Sequence)<br>EIVLTQSPATLSLSPGERATLSCRASQSVSSYLAWYQQKPGQAPRLLIYD<br>ASNRATGIPARFSGSGSGTDFTLTISSLEPEDFAVYYCQQSSNWPRTFGQ<br>GTKVEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGEC |

-continued

| Amino Acid and Nucleotide Sequences |
|---|
| SEQ ID NO: 32 (Pembrolizumab Heavy Chain) (Artificial Sequence)<br>QVQLVQSGVEVKKPGASVKVSCKASGYTFTNYYMYWVRQAPGQGLEWMGG<br>INPSNGGTNFNEKFKNRVTLTTDSSTTTAYMELKSLQFDDTAVYYCARRD<br>YRFDMGFDYWGQGTTVTVSSASTKGPSVFPLAPCSRSTSESTAALGCLVK<br>DYFPEPVTVSWNSGALTSGVHTFPAVLQSSGLYSLSSVVTVPSSSLGTKT<br>YTCNVDHKPSNTKVDKRVESKYGPPCPPCPAPEFLGGPSVFLFPPKPKDT<br>LMISRTPEVTCVVVDVSQEDPEVQFNWYVDGVEVHNAKTKPREEQFNSTY<br>RVVSVLTVLHQDWLNGKEYKCKVSNKGLPSSIEKTISKAKGQPREPQVYT<br>LPPSQEEMTKNQVSLTCLVKGFYPSDIAVEWESNGQPENNYKTTPPVLDS<br>DGSFFLYSRLTVDKSRWQEGNVFSCSVMHEALHNHYTQKSLSLSLGK |
| SEQ ID NO: 33 (Pembrolizumab Light Chain) (Artificial Sequence)<br>EIVLTQSPATLSLSPGERATLSCRASKGVSTSGYSYLHWYQQKPGQAPRL<br>LIYLASYLESGVPARFSGSGSGTDFTLTISSLEPEDFAVYYCQHSRDLPL<br>TFGGGTKVEIKRTVAAPSVFIFPPSDEQLKSGTASVVCLLNNFYPREAKV<br>QWKVDNALQSGNSQESVTEQDSKDSTYSLSSTLTLSKADYEKHKVYACEV<br>THQGLSSPVTKSFNRGEC |
| SEQ ID NO: 34 (Human PD-1) (*Homo Sapiens*)<br>MQIPQAPWPVVWAVLQLGWRPGWFLDSPDRPWNPPTFSPALLVVTEGDNA<br>TFTCSFSNTSESFVLNWYRMSPSNQTDKLAAFPEDRSQPGQDCRFRVTQL<br>PNGRDFHMSVVRARRNDSGTYLCGAISLAPKAQIKESLRAELRVTERRAE<br>VPTAHPSPSPRPAGQFQTLVVGVVGGLLGSLVLLVWVLAVICSRAARGTI<br>GARRTGQPLKEDPSAVPVFSVDYGELDFQWREKTPEPPVPCVPEQTEYAT<br>IVFPSGMGTSSPARRGSADGPRSAQPLRPEDGHCSWPL |

We claim:

1. A method of treating melanoma, lung cancer, head and neck cancer, colorectal cancer, pancreatic cancer, gastric cancer, kidney cancer, bladder cancer, prostate cancer, breast cancer, ovarian cancer, esophageal cancer, soft tissue sarcoma, or liver cancer comprising administering to a patient in need, thereof an effective amount of (a) an anti-human Tim-3 (SEQ ID NO: 1) antibody in simultaneous, separate, or sequential combination with an effective amount of an anti-human PD-1 (SEQ ID NO: 34) antibody; wherein the anti-human Tim-3 antibody comprises HCDR1 having the amino acid sequence of SEQ ID: 2, HCDR2 having the amino acid sequence of SEQ ID NO: 3, HCDR3 having the amino acid sequence of SEQ ID NO: 4, LCDR1 having the amino acid sequence of SEQ ID NO: 5, LCDR2 having the amino acid sequence of SEQ ID NO: 6, and LCDR3 having the amino acid sequence of SEQ ID NO: 7; and (b) wherein the anti-human PD-1 antibody comprises HCDR1 having the amino acid sequence of SEQ ID NO: 16, HCDR2 having the amino acid sequence of SEQ ID NO: 17, HCDR3 having the amino acid sequence of SEQ ID NO: 18, LCDR1 having the amino acid sequence of SEQ ID NO: 19, LCDR2 having the amino acid sequence of SEQ ID NO: 20, and LCDR3 having the amino acid sequence of SEQ ID NO: 21.

2. The method of claim 1, wherein the anti-human Tim-3 antibody comprises a heavy chain variable region having the amino acid sequence of SEQ ID NO: 8 and a light chain variable region having the amino acid sequence of SEQ ID NO: 9.

3. The method of claim 2, wherein the anti-human Tim-3 antibody comprises a heavy chain having the amino acid sequence of SEQ ID NO: 10 and a light chain having the amino acid sequence of SEQ ID NO: 11.

4. The method of claim 2, wherein the anti-human PD-1 antibody comprises a heavy chain variable region having the amino acid sequence of SEQ ID NO: 22 and a light chain variable region having the amino acid sequence of SEQ ID NO: 23.

5. The method of claim 4, wherein the anti-human PD-1 antibody comprises a heavy chain having the amino acid sequence of SEQ ID NO: 24 and a light chain having the amino acid sequence of SEQ ID NO: 26.

6. The method of claim 4, wherein the anti-human PD-1 antibody comprises a heavy chain having the amino acid sequence of SEQ ID NO: 25 and a light chain having the amino acid sequence of SEQ ID NO: 26.

7. The method of claim 1, wherein the lung cancer is non-small cell lung cancer.

8. The method of claim 3, wherein at least one of the anti-human Tim-3 antibody and anti-human PD-1 antibody is administered in simultaneous, separate, or sequential combination with ionizing radiation.

9. The method of claim 3, wherein at least one of the anti-human Tim-3 antibody and anti-human PD-1 antibody is administered in simultaneous, separate, or sequential combination with one or more chemotherapeutic agents.

10. The method of claim 3, wherein the anti-human PD-1 antibody comprises a heavy chain having the amino acid sequence of SEQ ID NO: 24 and a light chain having the amino acid sequence of SEQ ID NO: 26.

11. The method of claim 3, wherein the anti-human PD-1 antibody comprises a heavy chain having the amino acid sequence of SEQ ID NO: 25 and a light chain having the amino acid sequence of SEQ ID NO: 26.

* * * * *

SEQUENCE LISTING

<160> NUMBER OF SEQ ID NOS: 34

<210> SEQ ID NO 1
<211> LENGTH: 130
<212> TYPE: PRT
<213> ORGANISM: Human

<400> SEQUENCE: 1

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys
    130

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Ala Ala Ser Gly Phe Thr Phe Ser Ser Tyr Tyr Met Ser
1 5 10

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

Ala Ile Ser Gly Ser Gly Gly Ser Thr Tyr Tyr Ala Asp Ser Val Lys
1 5 10 15

Gly

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Ala Arg Tyr Ala Arg Thr Ala Phe Asp Leu
1 5 10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Gln Ala Ser Gln Asp Ile Tyr Asn Tyr Leu Asn
1 5 10

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Tyr Ala Ala Ser Ser Leu Gln Ser
1 5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Ala Asn Ser Phe Pro Pro Thr
1 5

<210> SEQ ID NO 8
<211> LENGTH: 117
<212> TYPE: PRT
<213> ORGANISM: Artificial Sequence
<220> FEATURE:

-continued

<223> OTHER INFORMATION: Synthetic Construct

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Arg Thr Ala Phe Asp Leu Trp Gly Gln Gly Thr Leu
            100                 105                 110

Val Thr Val Ser Ser
        115
```

<210> SEQ ID NO 9
<211> LENGTH: 107
<212> TYPE: PRT
<213> ORGANISM: Artificial Sequence
<220> FEATURE:
<223> OTHER INFORMATION: Synthetic Construct

<400> SEQUENCE: 9

```
Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys
            100                 105
```

<210> SEQ ID NO 10
<211> LENGTH: 447
<212> TYPE: PRT
<213> ORGANISM: Artificial Sequence
<220> FEATURE:
<223> OTHER INFORMATION: Synthetic Construct

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Ala Arg Thr Ala Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Glu Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 11
<211> LENGTH: 214
<212> TYPE: PRT
<213> ORGANISM: Artificial Sequence
<220> FEATURE:
<223> OTHER INFORMATION: Synthetic Construct

<400> SEQUENCE: 11

```
Asp Ile Val Met Thr Gln Ser Pro Ser Ser Leu Ser Ala Ser Val Gly
1               5                   10                  15

Asp Gly Val Thr Ile Thr Cys Gln Ala Ser Gln Asp Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 12
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 12

```
gaggtgcagc tgttggagtc tggcggaggg ctggtgcagc cgggaggcag cctcaggctg     60

agctgcgctg cgagcgggtt tactttctcg tcgtactata tgtcgtgggt gagacaagca    120

ccaggtaaag gacttgagtg ggtgtccgct atctcaggca gcggaggatc cacctactac    180

gcggattcag tcaagggaag attcactatc tcgcgcgaca attccaagaa caccctgtac    240

ctccagatga actcgctgcg ggcagaagat acggccgtgt actactgtgc ccgctacgcc    300

cggaccgcct tcgacttgtg gggtcaggga accctggtca ctgtctcctc agctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgcactga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

-continued

```
gacaaaactc acacatgccc accgtgccca gcacctgaag ccgagggggc accgtcagtc     720

ttcctcttcc ccccaaaacc caaggacacc ctcatgatct cccggacccc tgaggtcaca     780

tgcgtggtgg tggacgtgag ccacgaagac cctgaggtca agttcaactg gtatgtggac     840

ggcgtggagg tgcataatgc caagacaaag ccgcgggagg agcagtacaa cagcacgtac     900

cgtgtggtca gcgtcctcac cgtcctgcac caagactggc tgaatggcaa ggagtacaag     960

tgcaaggtct ccaacaaagc cctcccatcc tccatcgaga aaaccatctc caaagccaaa    1020

gggcagcccc gagaaccaca ggtgtacacc ctgcccccat cccgggagga gatgaccaag    1080

aaccaagtca gcctgacctg cctggtcaaa ggcttctatc ccagcgacat cgccgtggag    1140

tgggagagca atgggcagcc ggagaacaac tacaagacca cgcctcccgt gctggactcc    1200

gacggctcct tcttcctcta ttccaagctc accgtggaca agagcaggtg gcagcagggg    1260

aacgtcttct catgctccgt gatgcatgag gctctgcaca accactacac gcagaagagc    1320

ctctccctgt ctccgggcaa a                                              1341


<210> SEQ ID NO 13
<211> LENGTH: 642
<212> TYPE: DNA
<213> ORGANISM: Artificial Sequence
<220> FEATURE:
<223> OTHER INFORMATION: Synthetic Construct

<400> SEQUENCE: 13

gacatcgtga tgactcaaag cccttcaagc ctctcggcgt cagtcggtga tggcgtgacc      60

attacctgtc aagcatccca agacatctac aactacttga attggtacca gcagaagcca     120

gggaaagccc cgaagctgct gatctacgcc gcctcctcac ttcagagcgg agtgccatcc     180

cgcttttccg gatcggggag cggaacggat ttcactctga ccatctcgtc gctgcaaccg     240

gaggacttcg cgacttacta ttgccagcag gctaactcgt tcccgcccac tttcggacag     300

ggcaccaagc tcgaaatcaa acgaactgtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gt                        642


<210> SEQ ID NO 14
<211> LENGTH: 526
<212> TYPE: PRT
<213> ORGANISM: Human

<400> SEQUENCE: 14

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80
```

-continued

```
Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
```

```
            500                 505                 510

Leu Thr Ala Thr Glu Ile Ile Tyr Ser Glu Val Lys Lys Gln
        515                 520                 525


<210> SEQ ID NO 15
<211> LENGTH: 323
<212> TYPE: PRT
<213> ORGANISM: Human

<400> SEQUENCE: 15

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu Arg Asn Leu
    290                 295                 300

Pro Thr Ile Asn Arg Leu Glu Val Gly Gly Asp Ile Gln Leu Thr His
305                 310                 315                 320

Val Gln Thr


<210> SEQ ID NO 16
<211> LENGTH: 13
<212> TYPE: PRT
```

<213> ORGANISM: Artificial Sequence
<220> FEATURE:
<223> OTHER INFORMATION: Synthetic Construct

<400> SEQUENCE: 16

Lys Ala Ser Gly Gly Thr Phe Ser Ser Tyr Ala Ile Ser
1               5                   10

<210> SEQ ID NO 17
<211> LENGTH: 17
<212> TYPE: PRT
<213> ORGANISM: Artificial Sequence
<220> FEATURE:
<223> OTHER INFORMATION: Synthetic Construct

<400> SEQUENCE: 17

Leu Ile Ile Pro Met Phe Asp Thr Ala Gly Tyr Ala Gln Lys Phe Gln
1               5                   10                  15

Gly

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Ala Arg Ala Glu His Ser Ser Thr Gly Thr Phe Asp Tyr
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Arg Ala Ser Gln Gly Ile Ser Ser Trp Leu Ala
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ser Ala Ala Ser Ser Leu Gln Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Gln Ala Asn His Leu Pro Phe Thr
1               5

<210> SEQ ID NO 22
<211> LENGTH: 120

<212> TYPE: PRT
<213> ORGANISM: Artificial Sequence
<220> FEATURE:
<223> OTHER INFORMATION: Synthetic Construct

<400> SEQUENCE: 22

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser
        115                 120
```

<210> SEQ ID NO 23
<211> LENGTH: 107
<212> TYPE: PRT
<213> ORGANISM: Artificial Sequence
<220> FEATURE:
<223> OTHER INFORMATION: Synthetic Construct

<400> SEQUENCE: 23

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys
            100                 105
```

<210> SEQ ID NO 24
<211> LENGTH: 447
<212> TYPE: PRT
<213> ORGANISM: Artificial Sequence
<220> FEATURE:
<223> OTHER INFORMATION: Synthetic Construct

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
        35                  40                  45

Gly Leu Ile Ile Pro Met Phe Asp Thr Ala Gly Tyr Ala Gln Lys Phe
    50                  55                  60

Gln Gly Arg Val Ala Ile Thr Val Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Glu His Ser Ser Thr Gly Thr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 25
```

<211> LENGTH: 446
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Leu Ile Ile Pro Met Phe Asp Thr Ala Gly Tyr Ala Gln Lys Phe
50 55 60

Gln Gly Arg Val Ala Ile Thr Val Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ala Glu His Ser Ser Thr Gly Thr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Cys Ser Arg Ser Thr Ser Glu Ser Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Lys Thr Tyr Thr Cys Asn Val Asp His Lys
195 200 205

Pro Ser Asn Thr Lys Val Asp Lys Arg Val Glu Ser Lys Tyr Gly Pro
210 215 220

Pro Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser Gln Glu Asp Pro Glu
260 265 270

Val Gln Phe Asn Trp Tyr Val Asp Gly Val Glu Val His Asn Ala Lys
275 280 285

Thr Lys Pro Arg Glu Glu Gln Phe Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Gly Leu Pro Ser Ser Ile Glu Lys Thr Ile
325 330 335

Ser Lys Ala Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

```
Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
        435                 440                 445


<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn His Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 27

caagtgcagc tggtgcagtc cggcgctgag gtgaaaaaac ccggatcctc cgtcaaggtg      60

tcctgtaaag ccagcggcgg cacattcagc agctacgcca tctcctgggt gaggcaagct     120
```

```
cctggacagg gcctggaatg gatgggcctg atcatcccca tgttcgacac cgccggctac    180

gctcagaaat tccagggccg ggtcgccatt acagtggatg agagcaccag cacagcctac    240

atggagctca gctccctgag gagcgaagat accgccgtct actattgtgc ccgggctgag    300

catagcagca ccggcacctt cgactattgg ggccagggaa ccctggtcac agtgagctcc    360

gcttccacaa aaggccccag cgtgtttccc ctggcccctt gtagcaggtc cacctccgaa    420

agcacagccg ctctgggctg cctggtcaag gattacttcc ccgagcccgt gaccgtgtcc    480

tggaatagcg gcgctctcac atccggagtg catacctttc ctgccgtgct ccagtcctcc    540

ggcctgtact ccctgagctc cgtggtgacc gtcccttcca gctccctggg caccaagacc    600

tatacctgta acgtggacca caagccctcc aataccaagg tggataagcg ggtcgagtcc    660

aagtacggac cccccttgccc tccttgtcct gctcctgaat tcctcggcgg acctagcgtc    720

tttctcttcc cccccaagcc caaggatacc ctgatgatct ccaggacccc cgaggtgaca    780

tgcgtcgtgg tcgatgtgtc ccaggaggat cctgaagtgc agttcaactg gtacgtggac    840

ggcgtcgaag tgcataacgc caagaccaag cccagggagg agcagttcaa ctccacctat    900

cgggtggtga gcgtgctgac cgtgctgcat caggactggc tcaacggcaa agagtacaag    960

tgcaaggtct ccaacaaggg actcccctcc agcatcgaga agaccattag caaggccaaa   1020

ggccaaccca gggagcctca ggtatatacg ctgcccccca gccaggagga gatgaccaaa   1080

aaccaggtca gcctcacctg tctggtcaag ggcttctacc ctagcgacat tgctgtcgag   1140

tgggagagca acggccagcc cgagaacaac tataaaacca cccccccctgt cctggactcc   1200

gacggatcct tcttcctgta ctccaggctg acagtcgaca agtcccggtg gcaagaggga   1260

aacgtcttct cctgctccgt gatgcacgaa gctctccaca accactacac ccagaagagc   1320

ctcagcctgt ccctgggcaa atgatga                                        1347
```

<210> SEQ ID NO 28
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 28

```
caggtgcagc tggtccagtc aggggctgaa gtgaagaagc ccggcagctc cgtgaaggtg     60

tcttgcaagg ccagcggcgg aacattctcc agttacgcca tctcttgggt gcggcaggct    120

ccaggccagg gcctggagtg gatgggcctg atcatcccca tgttcgacac cgcccgggtat    180

gcccagaagt ttcagggcag agtggcaatc acagtggacg agagcacctc cacagcctac    240

atggagctgt ctagcctgag atccgaggat accgccgtgt attattgtgc ccgggccgaa    300

cacagctcta cagggacttt cgactactgg ggccagggca ccctggtgac agtgtcctct    360

gctagcacca agggcccatc ggtcttcccg ctcgcgccct gctccaggag cacctccgag    420

agcacagccg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacgaagacc    600

tacacctgca acgtagatca caagcccagc aacaccaagg tggacaagag agttgagtcc    660

aaatatggtc ccccatgccc accctgccca gcacctgagg ccgccggggg accatcagtc    720

ttcctgttcc ccccaaaacc caaggacact ctcatgatct cccggacccc tgaggtcacg    780

tgcgtggtgg tggacgtgag ccaggaagac cccgaggtcc agttcaactg gtatgttgat    840
```

```
ggcgtggagg tgcataatgc caagacaaag ccgcgggagg agcagttcaa cagcacgtac    900

cgtgtggtca gcgtcctcac cgtcctgcac caggactggc tgaacggcaa ggagtacaag    960

tgcaaggtct ccaacaaagg cctcccgtcc tccatcgaga aaaccatctc caaagccaaa   1020

gggcagcccc gagagccaca ggtgtacacc ctgcccccat cccaagaaga aatgaccaaa   1080

aaccaagtca gcctgacctg cctggtcaaa ggcttctacc ccagcgacat cgccgtggag   1140

tgggaaagca atgggcagcc ggagaacaac tacaagacca cgcctcccgt gctggactcc   1200

gacggctcct tcttcctcta ctcccgtcta accgtggaca agagcaggtg gcaggagggg   1260

aatgtcttct catgctccgt gatgcatgag gctctgcaca accactacac acagaagagc   1320

ctctccctgt ctctgggt                                                 1338


<210> SEQ ID NO 29
<211> LENGTH: 648
<212> TYPE: PRT
<213> ORGANISM: Artificial Sequence
<220> FEATURE:
<223> OTHER INFORMATION: Synthetic Construct

<400> SEQUENCE: 29

Gly Ala Cys Ala Thr Cys Cys Ala Gly Ala Thr Gly Ala Cys Ala Cys
1               5                   10                  15

Ala Gly Thr Cys Cys Cys Cys Thr Ala Gly Cys Thr Cys Cys Gly Thr
            20                  25                  30

Gly Thr Cys Cys Gly Cys Thr Thr Cys Cys Gly Thr Gly Gly Gly Ala
        35                  40                  45

Gly Ala Cys Ala Gly Gly Gly Thr Gly Ala Cys Ala Ala Thr Cys Ala
    50                  55                  60

Cys Ala Thr Gly Cys Ala Gly Gly Gly Cys Thr Thr Cys Cys Cys Ala
65                  70                  75                  80

Gly Gly Gly Cys Ala Thr Cys Ala Gly Cys Ala Gly Cys Thr Gly Gly
                85                  90                  95

Cys Thr Gly Gly Cys Thr Thr Gly Gly Thr Ala Thr Cys Ala Gly Cys
            100                 105                 110

Ala Gly Ala Ala Gly Cys Cys Cys Gly Gly Cys Ala Ala Gly Gly Cys
        115                 120                 125

Cys Cys Cys Cys Ala Ala Gly Cys Thr Gly Cys Thr Gly Ala Thr Cys
    130                 135                 140

Ala Gly Cys Gly Cys Thr Gly Cys Thr Ala Gly Cys Thr Cys Cys Cys
145                 150                 155                 160

Thr Gly Cys Ala Gly Thr Cys Cys Gly Gly Ala Gly Thr Gly Cys Cys
                165                 170                 175

Thr Thr Cys Cys Ala Gly Gly Thr Thr Cys Thr Cys Cys Gly Gly Cys
            180                 185                 190

Thr Cys Cys Gly Gly Ala Ala Gly Cys Gly Gly Cys Ala Cys Cys Gly
        195                 200                 205

Ala Cys Thr Thr Cys Ala Cys Cys Cys Thr Gly Ala Cys Cys Ala Thr
    210                 215                 220

Cys Thr Cys Cys Ala Gly Cys Cys Thr Gly Cys Ala Gly Cys Cys Cys
225                 230                 235                 240

Gly Ala Gly Gly Ala Cys Thr Thr Cys Gly Cys Cys Ala Cys Cys Thr
                245                 250                 255

Ala Cys Thr Ala Cys Thr Gly Cys Cys Ala Ala Cys Ala Gly Gly Cys
            260                 265                 270
```

```
Cys Ala Ala Cys Cys Ala Cys Cys Thr Gly Cys Cys Cys Thr Thr Cys
        275                 280                 285

Ala Cys Cys Thr Thr Cys Gly Gly Cys Gly Gly Cys Gly Gly Cys Ala
    290                 295                 300

Cys Cys Ala Ala Gly Gly Thr Gly Gly Ala Gly Ala Thr Cys Ala Ala
305                 310                 315                 320

Gly Ala Gly Gly Ala Cys Cys Gly Thr Gly Gly Cys Cys Gly Cys Cys
                325                 330                 335

Cys Cys Cys Thr Cys Cys Gly Thr Gly Thr Thr Cys Ala Thr Cys Thr
            340                 345                 350

Thr Thr Cys Cys Cys Cys Cys Cys Ala Gly Cys Gly Ala Cys Gly Ala
        355                 360                 365

Gly Cys Ala Gly Cys Thr Gly Ala Ala Gly Ala Gly Cys Gly Gly Cys
    370                 375                 380

Ala Cys Cys Gly Cys Cys Thr Cys Cys Gly Thr Gly Gly Thr Gly Thr
385                 390                 395                 400

Gly Cys Cys Thr Gly Cys Thr Gly Ala Ala Cys Ala Ala Cys Thr Thr
                405                 410                 415

Cys Thr Ala Thr Cys Cys Cys Cys Gly Gly Gly Ala Gly Gly Cys Cys
            420                 425                 430

Ala Ala Gly Gly Thr Gly Cys Ala Gly Thr Gly Gly Ala Ala Gly Gly
        435                 440                 445

Thr Cys Gly Ala Cys Ala Ala Thr Gly Cys Cys Cys Thr Gly Cys Ala
    450                 455                 460

Gly Ala Gly Cys Gly Gly Cys Ala Ala Cys Thr Cys Cys Cys Ala Gly
465                 470                 475                 480

Gly Ala Gly Ala Gly Cys Gly Thr Gly Ala Cys Cys Gly Ala Gly Cys
                485                 490                 495

Ala Gly Gly Ala Cys Ala Gly Cys Ala Ala Gly Gly Ala Cys Thr Cys
            500                 505                 510

Cys Ala Cys Cys Thr Ala Cys Thr Cys Cys Cys Thr Gly Ala Gly Cys
        515                 520                 525

Thr Cys Cys Ala Cys Cys Cys Thr Gly Ala Cys Ala Cys Thr Gly Thr
    530                 535                 540

Cys Cys Ala Ala Gly Gly Cys Cys Gly Ala Cys Thr Ala Cys Gly Ala
545                 550                 555                 560

Gly Ala Ala Gly Cys Ala Cys Ala Ala Gly Gly Thr Gly Thr Ala Cys
                565                 570                 575

Gly Cys Cys Thr Gly Cys Gly Ala Gly Gly Thr Gly Ala Cys Ala Cys
            580                 585                 590

Ala Cys Cys Ala Gly Gly Gly Cys Cys Thr Gly Ala Gly Cys Thr Cys
        595                 600                 605

Cys Cys Cys Cys Gly Thr Gly Ala Cys Cys Ala Ala Gly Thr Cys Cys
    610                 615                 620

Thr Thr Cys Ala Ala Cys Ala Gly Gly Gly Gly Cys Gly Ala Gly Thr
625                 630                 635                 640

Gly Cys Thr Gly Ala Thr Gly Ala
                645
```

<210> SEQ ID NO 30
<211> LENGTH: 440
<212> TYPE: PRT
<213> ORGANISM: Artificial Sequence
<220> FEATURE:

<223> OTHER INFORMATION: Synthetic Construct

<400> SEQUENCE: 30

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400
```

```
Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 31
<211> LENGTH: 214
<212> TYPE: PRT
<213> ORGANISM: Artificial Sequence
<220> FEATURE:
<223> OTHER INFORMATION: Synthetic Construct

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 32
<211> LENGTH: 447
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45
```

```
Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 33
<211> LENGTH: 218

-continued

<212> TYPE: PRT
<213> ORGANISM: Artificial Sequence
<220> FEATURE:
<223> OTHER INFORMATION: Synthetic Construct

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 34
<211> LENGTH: 288
<212> TYPE: PRT
<213> ORGANISM: Human

<400> SEQUENCE: 34

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu

-continued

```
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```